US012612353B2

(12) United States Patent
Biermann et al.

(10) Patent No.: US 12,612,353 B2
(45) Date of Patent: Apr. 28, 2026

(54) METHOD FOR THE PRODUCTION OF MUSK FRAGRANCE INGREDIENT

(71) Applicant: Givaudan SA, Vernier (CH)

(72) Inventors: Marc Biermann, Wallisellen (CH); Fabian Ruethi, Winterthur (CH); Marco Bocola, Sankt Augustin (DE); Haibin Chen, Ningbo (CN); Kuifang He, Ningbo (CN); Shumin Shi, Ningbo (CN)

(73) Assignee: GIVAUDAN SA, Vernier (CH)

( * ) Notice: Subject to any disclaimer, the term of this patent is extended or adjusted under 35 U.S.C. 154(b) by 658 days.

(21) Appl. No.: 18/017,264

(22) PCT Filed: Jul. 20, 2021

(86) PCT No.: PCT/CN2021/107393
§ 371 (c)(1),
(2) Date: Jan. 20, 2023

(87) PCT Pub. No.: WO2022/017389
PCT Pub. Date: Jan. 27, 2022

(65) Prior Publication Data
US 2024/0182395 A1 Jun. 6, 2024

(30) Foreign Application Priority Data
Jul. 21, 2020 (GB) ..................................... 2011259

(51) Int. Cl.
*C07C 49/385* (2006.01)
*C11B 9/00* (2006.01)
*C12N 9/04* (2006.01)
*C12P 7/26* (2006.01)
*C12P 17/08* (2006.01)

(52) U.S. Cl.
CPC .......... *C07C 49/385* (2013.01); *C11B 9/0038* (2013.01); *C11B 9/0084* (2013.01); *C12N 9/0006* (2013.01); *C12P 7/26* (2013.01); *C12P 17/08* (2013.01); *C12Y 101/01001* (2013.01)

(58) Field of Classification Search
CPC ................................ C07C 49/385; C11B 9/00
USPC .................................................. 512/27, 4, 1
See application file for complete search history.

(56) References Cited

U.S. PATENT DOCUMENTS

| | | | | |
|---|---|---|---|---|
| 9,896,644 | B2 | 2/2018 | Fankhauser et al. | |
| 2012/0196334 | A1 | 8/2012 | Chatterjee et al. | |
| 2017/0362153 | A1 | 12/2017 | Tanino et al. | |
| 2018/0346478 | A1* | 12/2018 | Werner ................ | C07D 493/06 |
| 2022/0119404 | A1* | 4/2022 | Kashiwagi ........... | C07D 493/08 |

FOREIGN PATENT DOCUMENTS

| | | | |
|---|---|---|---|
| EP | 3484844 | A1 | 5/2019 |
| EP | 3331843 | B1 | 3/2021 |
| WO | 2007076109 | A2 | 7/2007 |
| WO | 2017024126 | A1 | 2/2017 |
| WO | 2018011386 | A1 | 1/2018 |
| WO | 2020066898 | A1 | 4/2020 |

OTHER PUBLICATIONS

International Search Report for App. No. PCT/CN2021/107393 dated Oct. 22, 2021.
Written Opinion for App. No. PCT/CN2021/107393 dated Oct. 22, 2021.
Great Britain Search Report for App. No. 2011259.5 dated Dec. 22, 2020.
Baugh, et al., Chain A, short chain dehyrogenase, Jan. 27, 2018.
L. Baugh, et al., Chain A, short chain dehyrogenase, Jan. 27, 2018.
Product class 9: B-hydroxy carbonyl compounds; Science of Synthesis (2008) (Accession No. 151:147615 CASREACT).
V. de Berardinis et al., "Expanding the reaction space of aldolases using hydroxypyruvate as a nucleophilic substrate"; Green Chem, Nov. 18, 2016.

* cited by examiner

*Primary Examiner* — Jessica Whiteley
(74) *Attorney, Agent, or Firm* — Curatolo Sidoti & Trillis Co., LPA; Floyd Trillis, III; Salvatore A. Sidoti

(57) ABSTRACT

A method for making intermediate compounds suitable for making muscenone, the compositions made by said methods, the various uses of said compositions, and enzyme variants useful in said methods.

22 Claims, 1 Drawing Sheet

Specification includes a Sequence Listing.

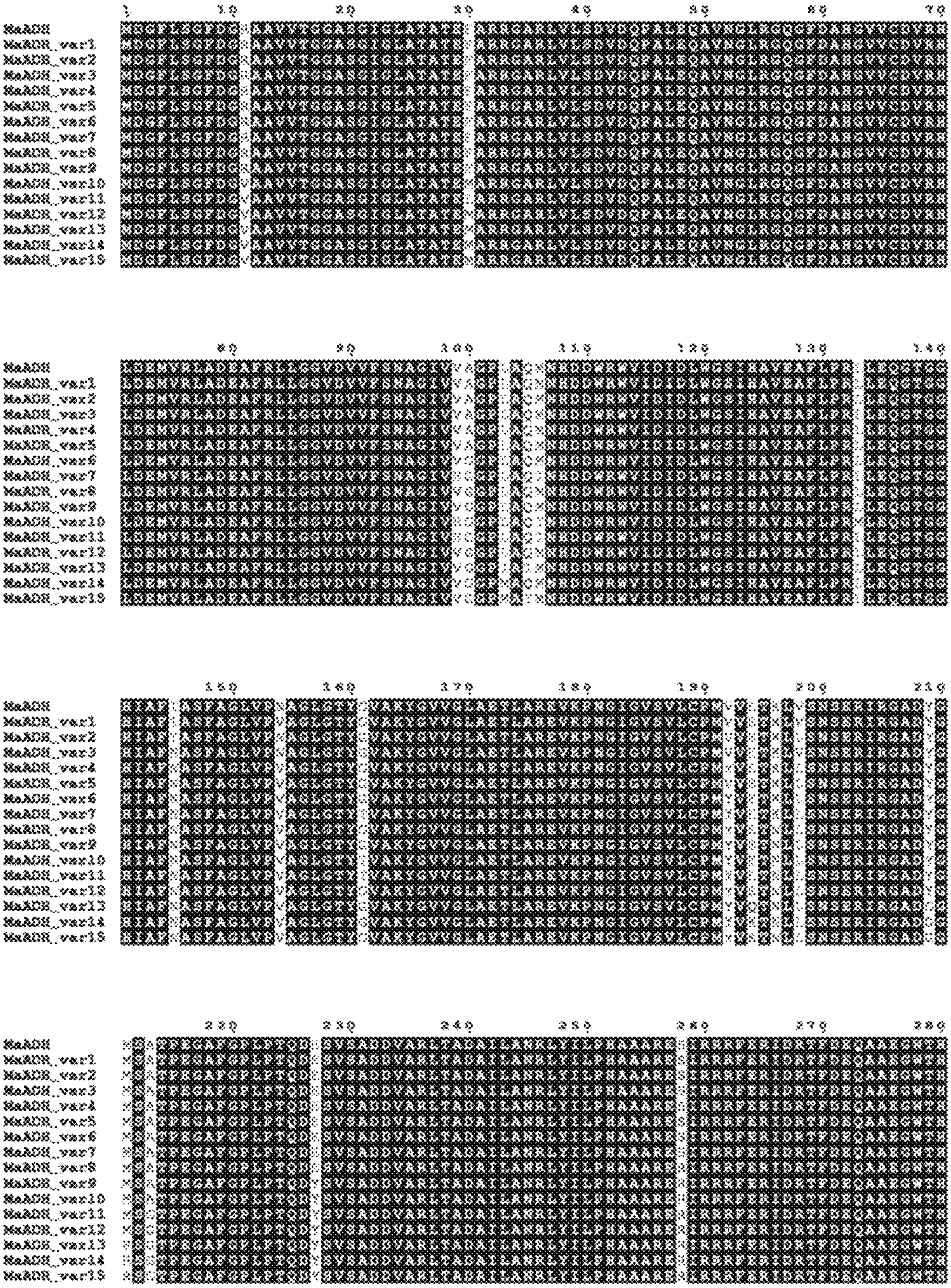

```
SEQUENCE LISTING


<160> NUMBER OF SEQ ID NOS: 16

<210> SEQ ID NO 1
<211> LENGTH: 280
<212> TYPE: PRT
<213> ORGANISM: Mycobacterium avium

<400> SEQUENCE: 1

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Thr Ala Ser Phe Ala Gly Leu Val Pro Asn Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Val Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
```

```
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 2
<211> LENGTH: 280
<212> TYPE: PRT
<213> ORGANISM: Escherichia coli

<400> SEQUENCE: 2

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Thr Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Val Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 3
<211> LENGTH: 280
<212> TYPE: PRT
<213> ORGANISM: Escherichia coli
```

<400> SEQUENCE: 3

```
Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Thr Ala Ser Phe Ala Gly Leu Val Pro Asn Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280
```

<210> SEQ ID NO 4
<211> LENGTH: 280
<212> TYPE: PRT
<213> ORGANISM: Escherichia coli

<400> SEQUENCE: 4

```
Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80
```

```
Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Asn Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Val Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 5
<211> LENGTH: 280
<212> TYPE: PRT
<213> ORGANISM: Escherichia coli

<400> SEQUENCE: 5

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175
```

```
Glu Val Lys Pro Asn Gly Ile Gly Val Ser Val Leu Cys Pro Met Tyr
            180                 185                 190

Val Glu Thr Lys Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 6
<211> LENGTH: 280
<212> TYPE: PRT
<213> ORGANISM: Escherichia coli

<400> SEQUENCE: 6

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
```

```
            260                 265                 270

Gln Ala Ala Glu Gly Trp Thr His
        275                 280


<210> SEQ ID NO 7
<211> LENGTH: 280
<212> TYPE: PRT
<213> ORGANISM: Escherichia coli

<400> SEQUENCE: 7

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 8
<211> LENGTH: 280
<212> TYPE: PRT
<213> ORGANISM: Escherichia coli

<400> SEQUENCE: 8

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
```

-continued

```
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Ala Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Val
            180                 185                 190

Val Glu Thr Lys Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Ser Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 9
<211> LENGTH: 280
<212> TYPE: PRT
<213> ORGANISM: Escherichia coli

<400> SEQUENCE: 9

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Gly Gly Pro Leu Ala Gln Met Asn His Asp Asp Trp Arg
            100                 105                 110
```

-continued

```
Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Tyr
            180                 185                 190

Val Glu Thr Asn Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Glu Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 10
<211> LENGTH: 280
<212> TYPE: PRT
<213> ORGANISM: Escherichia coli

<400> SEQUENCE: 10

Met Asp Gly Phe Leu Ser Gly Phe Asp Gly Arg Ala Ala Val Val Thr
1               5                   10                  15

Gly Gly Ala Ser Gly Ile Gly Leu Ala Thr Ala Thr Glu Phe Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Gly Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Tyr
            180                 185                 190

Val Glu Thr Asn Leu Leu Ser Asn Ser Glu Arg Ile Arg Gly Ala Asp
        195                 200                 205
```

-continued

```
Tyr Gly Met Ser Ala Thr Pro Glu Gly Ala Phe Gly Pro Leu Pro Thr
    210                 215                 220

Gln Asp Tyr Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 11
<211> LENGTH: 280
<212> TYPE: PRT
<213> ORGANISM: Escherichia coli

<400> SEQUENCE: 11

Met Asp Gly Phe Leu Ser Gly Phe Asp Gly Val Ala Ala Val Val Thr
1               5                   10                  15

Gly Gly Ala Ser Gly Ile Gly Leu Ala Thr Ala Thr Glu Met Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val His Gly Gly Pro Leu Ala Gln Thr Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Met Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Thr Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Tyr
            180                 185                 190

Val Glu Thr Asn Leu Leu Ser Asn Ser Glu Arg Ile Arg Gly Ala Asp
        195                 200                 205

Tyr Gly Met Ser Ala Thr Pro Glu Gly Ala Phe Gly Pro Leu Pro Thr
    210                 215                 220

Gln Asp Tyr Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280
```

-continued

<210> SEQ ID NO 12
<211> LENGTH: 280
<212> TYPE: PRT
<213> ORGANISM: Escherichia coli

<400> SEQUENCE: 12

```
Met Asp Gly Phe Leu Ser Gly Phe Asp Gly Val Ala Ala Val Val Thr
1               5                   10                  15

Gly Gly Ala Ser Gly Ile Gly Leu Ala Thr Ala Thr Glu Leu Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val His Gly Gly Pro Leu Ala Gln Thr Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Thr Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Tyr
            180                 185                 190

Val Glu Thr Asn Leu Leu Ser Asn Ser Glu Arg Ile Arg Gly Ala Asp
        195                 200                 205

Tyr Gly Met Ser Gly Thr Pro Glu Gly Ala Phe Gly Pro Leu Pro Thr
    210                 215                 220

Gln Asp Tyr Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280
```

<210> SEQ ID NO 13
<211> LENGTH: 280
<212> TYPE: PRT
<213> ORGANISM: Escherichia coli

<400> SEQUENCE: 13

```
Met Asp Gly Phe Leu Ser Gly Phe Asp Gly Val Ala Ala Val Val Thr
1               5                   10                  15

Gly Gly Ala Ser Gly Ile Gly Leu Ala Thr Ala Thr Glu Met Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
```

```
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Gly Gly Pro Leu Ala Gln Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Tyr
            180                 185                 190

Val Glu Thr Asn Leu Leu Ser Asn Ser Glu Arg Ile Arg Gly Ala Asp
        195                 200                 205

Tyr Gly Met Ser Gly Thr Pro Glu Gly Ala Phe Gly Pro Leu Pro Thr
    210                 215                 220

Gln Asp Tyr Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 14
<211> LENGTH: 280
<212> TYPE: PRT
<213> ORGANISM: Escherichia coli

<400> SEQUENCE: 14

Met Asp Gly Phe Leu Ser Gly Phe Asp Gly Val Ala Ala Val Val Thr
1               5                   10                  15

Gly Gly Ala Ser Gly Ile Gly Leu Ala Thr Ala Thr Glu Met Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Gly Gly Pro Ile Ala Thr Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140
```

-continued

Asn Ala Ser Phe Ala Gly Leu Val Pro Val Ala Gly Leu Gly Thr Tyr
145 150 155 160

Gly Val Ala Lys Tyr Gly Val Val Gly Leu Ala Glu Thr Leu Ala Arg
165 170 175

Glu Val Lys Pro Asn Gly Ile Gly Val Ser Val Leu Cys Pro Met Tyr
180 185 190

Val Gln Thr Asn Leu Leu Ser Asn Ser Glu Arg Ile Arg Gly Ala Asp
195 200 205

Gly Gly Pro Ser Gly Thr Pro Glu Gly Ala Phe Gly Pro Leu Pro Thr
210 215 220

Gln Asp Tyr Ser Val Ser Ala Asp Asp Val Ala Arg Leu Thr Ala Asp
225 230 235 240

Ala Ile Leu Ala Asn Arg Leu Tyr Ile Leu Pro His Ala Ala Ala Arg
245 250 255

Glu Arg Ile Arg Arg Arg Phe Glu Arg Ile Asp Arg Thr Phe Asp Glu
260 265 270

Gln Ala Ala Glu Gly Trp Thr His
275 280

<210> SEQ ID NO 15
<211> LENGTH: 280
<212> TYPE: PRT
<213> ORGANISM: Escherichia coli

<400> SEQUENCE: 15

Met Asp Gly Phe Leu Ser Gly Phe Asp Gly Val Ala Ala Val Val Thr
1 5 10 15

Gly Gly Ala Ser Gly Ile Gly Leu Ala Thr Ala Thr Glu Met Ala Arg
20 25 30

Arg Gly Ala Arg Leu Val Leu Ser Asp Val Asp Gln Pro Ala Leu Glu
35 40 45

Gln Ala Val Asn Gly Leu Arg Gly Gln Gly Phe Asp Ala His Gly Val
50 55 60

Val Cys Asp Val Arg His Leu Asp Glu Met Val Arg Leu Ala Asp Glu
65 70 75 80

Ala Phe Arg Leu Leu Gly Gly Val Asp Val Val Phe Ser Asn Ala Gly
85 90 95

Ile Val Val Gly Gly Pro Met Ala Gln Met Asn His Asp Asp Trp Arg
100 105 110

Trp Val Ile Asp Ile Asp Leu Trp Gly Ser Ile His Ala Val Glu Ala
115 120 125

Phe Leu Pro Arg Leu Leu Glu Gln Gly Thr Gly Gly His Ile Ala Phe
130 135 140

Asn Ala Ser Phe Ala Gly Leu Val Pro Val Ala Gly Leu Gly Thr Tyr
145 150 155 160

Gly Val Ala Lys Tyr Gly Val Val Gly Leu Ala Glu Thr Leu Ala Arg
165 170 175

Glu Val Lys Pro Asn Gly Ile Gly Val Ser Val Leu Cys Pro Met Tyr
180 185 190

Val Lys Thr Asn Leu Leu Ser Asn Ser Glu Arg Ile Arg Gly Ala Asp
195 200 205

Gly Gly Arg Ser Gly Thr Pro Glu Gly Ala Phe Gly Pro Leu Pro Thr
210 215 220

Gln Asp Tyr Ser Val Ser Ala Asp Asp Val Ala Arg Leu Thr Ala Asp
225 230 235 240

-continued

```
Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280


<210> SEQ ID NO 16
<211> LENGTH: 280
<212> TYPE: PRT
<213> ORGANISM: Escherichia coli

<400> SEQUENCE: 16

Met Asp Gly Phe Leu Ser Gly Phe Asp Gly Val Ala Ala Val Val Thr
1               5                   10                  15

Gly Gly Ala Ser Gly Ile Gly Leu Ala Thr Ala Thr Glu Met Ala Arg
            20                  25                  30

Arg Gly Ala Arg Leu Val Leu Ser Asp Val Asp Gln Pro Ala Leu Glu
        35                  40                  45

Gln Ala Val Asn Gly Leu Arg Gly Gln Gly Phe Asp Ala His Gly Val
    50                  55                  60

Val Cys Asp Val Arg His Leu Asp Glu Met Val Arg Leu Ala Asp Glu
65                  70                  75                  80

Ala Phe Arg Leu Leu Gly Gly Val Asp Val Val Phe Ser Asn Ala Gly
                85                  90                  95

Ile Val Val Gly Gly Pro Met Ala Thr Met Asn His Asp Asp Trp Arg
            100                 105                 110

Trp Val Ile Asp Ile Asp Leu Trp Gly Ser Ile His Ala Val Glu Ala
        115                 120                 125

Phe Leu Pro Arg Leu Leu Glu Gln Gly Thr Gly Gly His Ile Ala Phe
    130                 135                 140

Asn Ala Ser Phe Ala Gly Leu Val Pro Val Ala Gly Leu Gly Thr Tyr
145                 150                 155                 160

Gly Val Ala Lys Tyr Gly Val Val Gly Leu Ala Glu Thr Leu Ala Arg
                165                 170                 175

Glu Val Lys Pro Asn Gly Ile Gly Val Ser Val Leu Cys Pro Met Tyr
            180                 185                 190

Val Lys Thr Asn Leu Leu Ser Asn Ser Glu Arg Ile Arg Gly Ala Asp
        195                 200                 205

Gly Gly Arg Ser Gly Thr Pro Glu Gly Ala Phe Gly Pro Leu Pro Thr
    210                 215                 220

Gln Asp Tyr Ser Val Ser Ala Asp Asp Val Ala Arg Leu Thr Ala Asp
225                 230                 235                 240

Ala Ile Leu Ala Asn Arg Leu Tyr Ile Leu Pro His Ala Ala Ala Arg
                245                 250                 255

Glu Arg Ile Arg Arg Arg Phe Glu Arg Ile Asp Arg Thr Phe Asp Glu
            260                 265                 270

Gln Ala Ala Glu Gly Trp Thr His
        275                 280
```

METHOD FOR THE PRODUCTION OF MUSK FRAGRANCE INGREDIENT

CROSS REFERENCE TO RELATED APPLICATIONS

This application is a national stage application of International Application No. PCT/CN2021/107393, filed 20 Jul. 2021, which claims priority from Great Britain Patent Application No. 2011259.5, filed 21 Jul. 2020, which applications are incorporated herein by reference.

TECHNICAL FIELD

The present invention relates generally to an enzymatic method for making intermediate compounds that can subsequently be used to make muscenone. The present invention further relates to a method for making muscenone comprising the enzymatic method for making said intermediate compounds. The present invention further relates to compositions comprising said intermediate compounds and compositions comprising various stereoisomers of muscenone. The present invention also relates to the use of said compositions as fragrance ingredients, for example in consumer products.

BACKGROUND

Muscenone is a fragrance ingredient used to provide a nitromusk powdery type of odor reminiscent of musk ketone.

Muscenone may also be referred to as 3-methyl cyclopentadecenone and has the structure shown in formula (V), Formula (V)

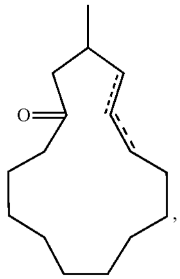

wherein one of is a single bond and the other is a double bond.

The compound of formula (V) has numerous stereoisomers. The double bond (at the 4- and 5-positions) may be in either E- or Z-configuration. In addition, different enantiomers of the compound of formula (V) exist due to the methyl group at the 3-position being in either (R) or (S) orientation. It is noted that the enantiomers (R)-5-Z-, (R)-5-E-, (S)-4-Z, and (S)-4-E are in the same orientation but the enantiomer changes from (R) to (S) when moving the double bond from the 5-position to the 4-position due to the change in prioritization in CIP nomenclature.

A number of multi-step methods for chemically synthesizing muscenone are known. However, it is desirable to provide alternative or improved methods that may, for example, be simplified and/or more environmentally friendly and/or more selective for monoreduction.

SUMMARY

In accordance with a first aspect of the present invention there is provided a method for making one or more of a compound of formula (II), a compound of formula (III) and a compound of formula (IV), Formula (II)

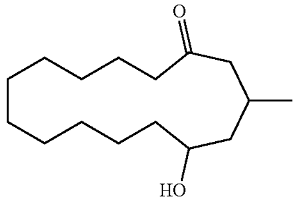

Formula (III)

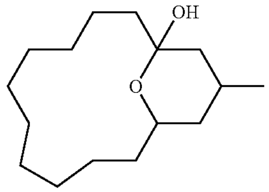

Formula (IV)

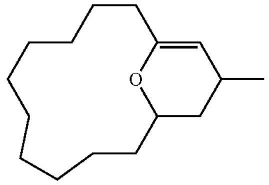

wherein the method comprises contacting a compound of formula (I) with an alcohol dehydrogenase, Formula (I)

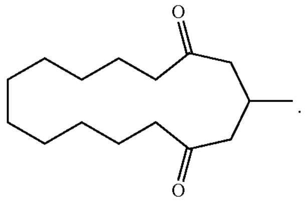

In certain embodiments, the method is for making two or three of a compound of formula (II), a compound of formula (III), and a compound of formula (IV). Thus, in certain embodiments, the method provides a mixture comprising a compound of formula (II), a compound of formula (III), and a compound of formula (IV).

In certain embodiments, the method further comprises treating the one or more of a compound of formula (II), a compound of formula (III), and a compound of formula (IV) with an acid to provide one or more compound(s) of formula (V), Formula (V)

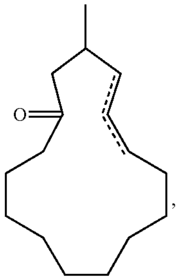

wherein one of  is a single bond and the other is a double bond.

In certain embodiments, the method further comprises treating a mixture comprising a compound of formula (II), a compound of formula (III), and a compound of formula (IV) with an acid to provide a mixture comprising a compound of formula (Va), a compound of formula (Vb), and a compound of formula (Vc), Formula (Va)

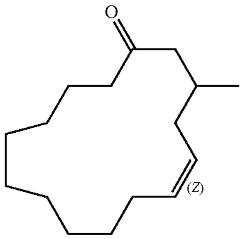

Formula (Vb)

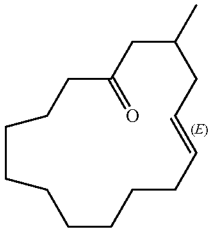

Formula (Vc)

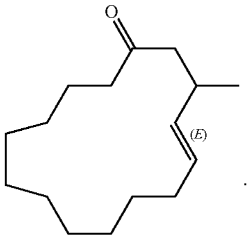

In certain embodiments, the acidic treatment provides a mixture comprising a compound of formula (Va), a compound of formula (Vb), a compound of formula (Vc), and a compound of formula (Vd), Formula (Vd)

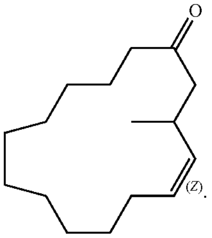

In certain embodiments, the treating with an acid provides a mixture that does not comprise a compound of formula (Vd).

In accordance with a second aspect of the present invention there is provided a composition comprising a compound of formula (II), a compound of formula (III), and a compound of formula (IV).

In accordance with a third aspect of the present invention there is provided a composition comprising a compound of formula (Va), a compound of formula (Vb), and a compound of formula (Vc), wherein:

- the compound of formula (Va) is present in the composition in an amount ranging from about 20.0 wt % to less than about 40.0 wt %;
- the compound of formula (Vb) is present in the composition in an amount ranging from greater than about 40.0 wt % to about 70.0 wt %; and
- the compound of formula (Vc) is present in the composition in an amount ranging from about 5.0 wt % to about 15.0 wt %.

In certain embodiments the compound of formula (Va) has an enantiomeric excess of the (R) enantiomer equal to or greater than about 25.0%; and/or the compound of formula (Vb) has an enantiomeric excess of the (R) enantiomer equal to or greater than about 25.0%; and/or the compound of formula (Vc) has an enantiomeric excess of the (S) enantiomer equal to or greater than about 25.0%.

In certain embodiments the compound of formula (Va) has an enantiomeric excess of the (R) enantiomer equal to or greater than about 60.0%; and/or the compound of formula (Vb) has an enantiomeric excess of the (R) enantiomer equal to or greater than about 60.0%; and/or the compound of formula (Vc) has an enantiomeric excess of the (S) enantiomer equal to or greater than about 60.0%.

In certain embodiments, the composition of the third aspect of the present invention further comprises a compound of formula (Vd) in an amount ranging from about 0.5 wt % to about 5.0 wt %. In certain embodiments, the composition of the third aspect of the present invention does not comprise a compound of formula (Vd).

In accordance with a fourth aspect of the present invention there is provided a composition comprising:

- from 35 to 55% w/w of a compound of formula (Va) having an enantiomeric excess of the (R) enantiomer of less than 80%;
- from 27 to 40% w/w of a compound of formula (Vb) having an enantiomeric excess of the (R) enantiomer of less than 80%;
- from 3 to 20% w/w of a compound of formula (Vc) having an enantiomeric excess of the (S) enantiomer of less than 80%; and
- from 0 to 5% w/w of a compound of formula (Vd) having an enantiomeric excess of the (S) enantiomer of less than 80%.

In accordance with a fifth aspect of the present invention there is provided a composition obtained by and/or obtainable by a method of the first aspect of the present invention. The composition may, for example, be in accordance with the composition of the second aspect of the present invention or the composition of the third aspect of the present invention.

In accordance with a sixth aspect of the present invention there is provided a use of a composition of the second, third or fourth aspect of the present invention as a fragrance ingredient.

In accordance with a seventh aspect of the present invention there is provided a consumer product comprising a composition of the third or fourth aspect of the present invention.

In accordance with an eight aspect of the present invention there is provided an alcohol dehydrogenase, the alcohol dehydrogenase being a variant of the alcohol dehydrogenase having the amino acid sequence as set out in SEQ ID NO: 1, wherein the variant has at least 70% sequence identity with SEQ ID NO: 1. The alcohol dehydrogenase variant of the eight aspect is particularly useful in the methods of the other aspects of the present invention.

Certain embodiments of the present invention may provide one or more of the following advantages:

- simplified method for making muscenone with fewer steps;
- more environmentally friendly and sustainable method for making muscenone;
- more efficient method for making muscenone;
- less waste production when making muscenone;
- use of only environmentally friendly solvents;
- stereospecific method for making muscenone;
- production of enantioenriched muscenone;
- improved selectivity for monoreduction;
- high yield of muscenone.

Certain embodiments of the eight aspect of the present invention may provide one or more of the following advantages:

- to increase the substrate concentration and/or to decrease the enzyme concentration in the bioconversion of the present invention;
- to increase the isopropanol compatibility in the bioconversion of the present invention;
- to maintain the low diol formation in the bioconversion of the present invention;
- to increase the amount of (Z)-5-muscenone resulting from the acidification of the product of the bioconversion; and
- to increase the ee value of the R-enantiomer of (Z)-5-muscenone resulting from the acidification of the product of the bioconversion.

The details, examples and preferences provided in relation to any particular one or more of the stated aspects of the present invention will be further described herein and apply equally to all aspects of the present invention. Any combination of the embodiments, examples and preferences described herein in all possible variations thereof is encompassed by the present invention unless otherwise indicated herein, or otherwise clearly contradicted by context.

BRIEF DESCRIPTION OF THE DRAWINGS

FIG. 1 shows a comparison of the amino acid sequences as set out in SEQ ID NO: 1 to 16.

DETAILED DESCRIPTION

The present invention is based, at least in part, on the surprising finding that an alcohol dehydrogenase enzyme can be used to convert the macrocyclic diketone of formula (I) into intermediate compounds (bioconversion reaction), Formula (I)

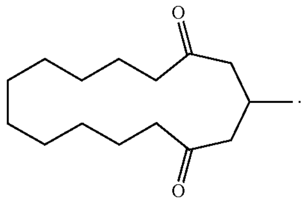

The intermediate compounds typically comprise a mixture of hydroxy ketone, hemi acetal and enol ether compounds. The intermediate compounds can then be converted into muscenone of formula (V) by treatment with acid, causing a dehydration and/or rearrangement of the intermediate compounds to form a compound of formula (V), Formula (V)

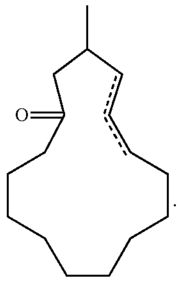

The present invention is further based on the surprising finding that an alcohol dehydrogenase enzyme can be used to provide compositions that are enriched in certain stereoisomers of muscenone of formula (V).

Bioconversion Reaction

There is provided herein a method for making one or more of a compound of formula (II), a compound of formula (III) and a compound of formula (IV), Formula (II)

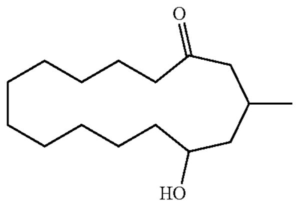

Formula (III)

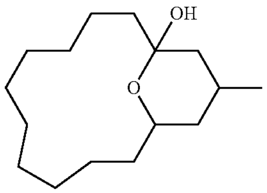

-continued

Formula (IV)

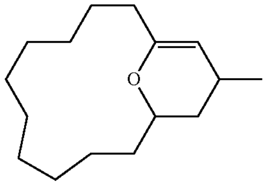

wherein the method comprises contacting a compound of formula (I) with an alcohol dehydrogenase, Formula (I)

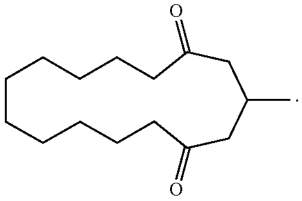

The compound of formula (I) may be referred to as 3-methylcyclopentadecane-1,5-dione. The compound of formula (I) is commercially available or may be prepared by methods known to persons of ordinary skill in the art, for example the methods described in *Helvetica Chimica Acta* 1967, 50, 705, or in WO 2016/104474 or in WO 2016/184948, the contents of which are incorporated herein by reference.

The method may, for example, provide two or three of a compound of formula (II), a compound of formula (III), and a compound of formula (IV). For example, the method may provide a mixture comprising a compound of formula (II) and a compound of formula (III). For example, the method may provide a mixture comprising a compound of formula (III) and a compound of formula (IV). For example, the method may provide a mixture comprising a compound of formula (II) and a compound of formula (IV). For example, the method may provide a mixture comprising a compound of formula (II), a compound of formula (III), and a compound of formula (IV).

The method may, for example, provide further reaction products such as a compound of formula (VII), Formula (VII)

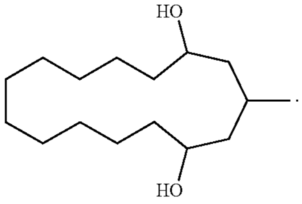

Therefore, the method may provide a mixture comprising one or more of a compound of formula (II), a compound of formula (III), a compound of formula (IV) and a compound of formula (VII).

The method may provide a mixture comprising one or more of a compound of formula (II), a compound of formula (III), a compound of formula (IV) and a compound of formula (VII), and wherein the compound of formula (VII) when present is present in an amount of 5% or less, 4% or less, 3% or less, 2% or less or 1% or less based on the relative plot area analysis generated by gas chromatography of the mixture. The method may provide a mixture comprising one or more of a compound of formula (II), a compound of formula (III) and a compound of formula (IV), wherein the mixture is substantially free of a compound of formula (VII).

The reaction may or may not proceed to completion. Therefore, the product of the bioconversion reaction (e.g. mixture comprising a compound of formula (II), a compound of formula (III), and a compound of formula (IV)) may further comprise unreacted compound of formula (I). Any unreacted compound of formula (I) could be removed from the composition before use as a fragrance ingredient. Alternatively, unreacted compound of formula (I) can remain in the composition for use as fragrance ingredient.

At least a portion of the compound of formula (II) and/or the compound of formula (III) made by the method may, for example, be converted to a compound of formula (IV) under the bioconversion reaction conditions prior to any acid treatment step described herein. Thus, the final product of the bioconversion reaction may particularly comprise a compound of formula (IV). For example, the final product of the bioconversion reaction may comprise a greater amount of a compound of formula (IV) compared to a compound of formula (II) and/or compared to a compound of formula (III). Where all of the compound of formula (II) and the compound of formula (III) have been converted to the compound of formula (IV), the final product of bioconversion reaction may not comprise any compound of formula (II) and/or any compound of formula (III).

As used herein, the term "alcohol dehydrogenase" (ADH) refers to a group of dehydrogenase enzymes (E.C. 1.1.1.1) that can convert ketone groups to alcohol groups. The term "alcohol dehydrogenase" may, for example, be used interchangeably with the terms "keto reductase" or "aldo-keto reductase" or "carbonyl reductase".

The alcohol dehydrogenase may, for example, be a wild-type ADH enzyme that is naturally occurring in a prokaryote or eukaryote. The alcohol dehydrogenase may, for example, be a variant of a wild-type alcohol dehydrogenase. As used herein, the term "variant" is to be understood as a polypeptide which differs in comparison to the polypeptide from which it is derived by one or more changes in the amino acid sequence. The polypeptide from which a variant is derived is also known as the parent or reference polypeptide. Typically a variant is constructed artificially, preferably by gene-technological means. The changes in the amino acid sequence may be amino acid exchanges (substitutions), insertions, deletions, N-terminal truncations, or C-terminal truncations, or any combination of these changes, which may occur at one or several sites.

The alcohol dehydrogenase may, for example, be a member of the short-chain dehydrogenases/reductases (SDR) superfamily, particularly a NAD- or NADP-dependent member of the SDR superfamily. Alcohol dehydrogenases that are members of the SDR superfamily may, for example, comprise about 250 to about 300 amino acid residues.

A suitable source of an alcohol dehydrogenase for use in the presently described methods may, for example, be *Mycobacterium avium*. For example, the alcohol dehydrogenase used in the presently described methods may be a wild-type alcohol dehydrogenase from *Mycobacterium avium* (e.g. an alcohol dehydrogenase having the amino acid sequence of SEQ ID NO: 1).

Functional homologues of the alcohol dehydrogenase enzymes may also be suitable for use in the bioconversion reaction described herein. A functional homologue is a polypeptide that has sequence similarity to a reference polypeptide (e.g. an alcohol dehydrogenase) and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild-type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional homologs described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide. Functional homologs can be identified by analysis of nucleotide and polypeptide sequence alignments. For example, performing a query on a database of nucleotide or polypeptide sequences can identify homologs of the nucleic acid sequences encoding the alcohol dehydrogenase derivative polypeptides and the like.

Hybridization can also be used to identify functional homologs and/or as a measure of homology between two nucleic acid sequences. A nucleic acid sequence encoding any alcohol dehydrogenase, or a portion thereof, can be used as a hybridization probe according to standard hybridization techniques. The hybridization of a probe to DNA or RNA from a test source (e.g. a mammalian cell) is an indication of the presence of the relevant DNA or RNA in the test source. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C. followed by a wash in 1×SSC, 0.1% SDS at 50° C. Highly stringent conditions are defined as equivalent to hybridization in 6× sodium chloride/sodium citrate (SSC) at 45° C. followed by a wash in 0.2×SSC, 0.1% SDS at 65° C. Sequence analysis to identify functional homologs can also involve BLAST, Reciprocal BLAST, or PSI-BLAST analysis of non-redundant databases using a relevant amino acid sequence as the reference sequence. Amino acid sequence is, in some instances, deduced from the nucleotide sequence. Those polypeptides in the database that have greater than 40% sequence identity are candidates for further evaluation for suitability for use in the bioconversion reaction described herein. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have for e.g. conserved functional domains.

The reference sequence may, for example, be a wild-type alcohol dehydrogenase from *Mycobacterium avium* (e.g. an alcohol dehydrogenase having the amino acid sequence of SEQ ID NO: 1).

Typically, polypeptides that exhibit at least about 30% amino acid sequence identity are useful to identify conserved regions. Conserved regions of related polypeptides exhibit at least 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, amino acid sequence identity. In some embodiments, a conserved region exhibits at least, 70%, 71%, 72%, 73%, 74%, 75%, 76%, 77%, 78%, 79%, 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity. Sequence identity can be determined as set forth above and below.

"Percent (%) identity" with respect to the amino acid sequence of a protein or enzyme is defined as the percentage of amino acids in a candidate protein or enzyme sequence that is identical with the amino acids in the protein or enzyme sequence, after aligning the sequence and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared. The terms "polypeptide" and "protein" are used interchangeably herein and mean any peptide-linked chain of amino acids, regardless of length or post-translational modification.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available eg. on https://www.ebi.ac.uk/Tools/msa/clustalo/ or the GAP program (mathematical algorithm of the University of Iowa) or the mathematical algorithm of Myers and Miller (1989—Cabios 4: 11-17). Preferred parameters used are the default parameters as they are set on https://www.ebi.ac.uk/Tools/msa/clustalo/.

Percentage sequence identity may be calculated using, for example, BLAST, BLAT or BlastZ (or BlastX). A similar algorithm is incorporated into the BLASTN and BLASTP programs of Altschul et al (1990) J. Mol. Biol. 215, 403-410. BLAST polynucleotide searches may be performed with the BLASTN program, score=100, word length=12, to obtain polynucleotide sequences that are homologous to those nucleic acids which encode the relevant protein. BLAST protein searches may be performed with the BLASTP program, score=50, word length=3, to obtain amino acid sequences homologous to the polypeptide.

To obtain gapped alignments for comparative purposes, Gapped BLAST may be utilized as described in Altschul et al (1997) Nucleic Acids Res. 25, 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1: 154-162) or Markov random fields. When percentages of sequence identity are referred to in the present application, these percentages are calculated in relation to the full length of the longer sequence, if not specifically indicated otherwise.

In particular embodiments, % identity between two sequences is determined using CLUSTAL O (version 1.2.4).

The alcohol dehydrogenase may, for example, accept the diketone compound of formula (I) as its substrate and may not accept the hydroxyketone compound of formula (II) as its substrate. As the diketone compound of formula (I) is symmetrical, a 100% theoretical yield may be achieved with high enantiomeric excess.

The alcohol dehydrogenase may, for example, be stereoselective for the (R) or (S) enantiomers described herein (enantiomers of the compounds of formula (II), (III) and (IV) having (R) or (S) configuration at the C-atom bearing the methyl group). In particular, the alcohol dehydrogenase may be stereoselective for the intermediates having (R) configuration at the C-atom bearing the methyl group. By stereoselective it is meant that a greater amount of either the (R) or (S) enantiomer is made compared to the other of the (R) and (S) enantiomer. This is surprising given the stereocenter of interest (which is the C-atom bearing the methyl group in the intermediate compounds, and which corresponds to the methyl at the C3-position in the compound of formula (V)) is in a beta-position to the ketone (i.e. two carbons away from the carbonyl where the reaction takes place). Thus, the products of the bioconversion reaction described herein may be enantiomer enriched, which may, for example, lead to an enantiomer enriched muscenone product after the acid treatment step described herein.

The alcohol dehydrogenase used in the presently described methods may, for example, be based on the amino acid sequence of SEQ ID NO: 1 or a variant, homologue, mutant, derivative or fragment thereof. The alcohol dehydrogenase used in the presently described methods may, for example, have an amino acid sequence with at least about 50% or at least about 55% or at least about 60% or at least about 65% or at least about 70% or at least about 75% or at least about 80% or at least about 85% or at least about 90% or at least about 95% or at least about 96% or at least about 97% or at least about 98% or at least about 99% sequence identity to SEQ ID NO: 1. The alcohol dehydrogenase used in the presently described methods may, for example, have equal to or less than about 100% or equal to or less than about 99% or equal to or less than about 98% sequence identity to SEQ ID NO: 1. Sequence identity may be determined as described above.

The alcohol dehydrogenase used in the presently described methods may, for example, exhibit up to about 60 amino acid alterations (e.g. substitutions, insertions, deletions, N-terminal truncations and/or C-terminal truncations) compared to a reference amino acid sequence (e.g. compared to SEQ ID NO: 1). For example, the alcohol dehydrogenase used in the presently described methods may exhibit up to about 55 or up to about 50 or up to about 45 or up to about 40 or up to about 35 or up to about 30 or up to about 25 or up to about 20 or up to about 15 or up to about 10 or up to about 5 or up to about 4 or up to about 3 or up to about 2 or up to about 1 amino acid alterations compared to a reference amino acid sequence (e.g. compared to SEQ ID NO: 1). The amino acid exchanges may be conservative and/or non-conservative.

Conservative amino acid substitutions may be made, for instance, on the basis of similarity in polarity, charge, size, solubility, hydrophobicity, hydrophilicity, and/or the amphipathic nature of the amino acid residues involved. The 20 naturally occurring amino acids as outlined above can be grouped into the following six standard amino acid groups:

(1) hydrophobic: Met, Ala, Val, Leu, Ile;

(2) neutral hydrophilic: Cys, Ser, Thr; Asn, Gln;

(3) acidic: Asp, Glu;

(4) basic: His, Lys, Arg;

(5) residues that influence chain orientation: Gly, Pro; and (6) aromatic: Trp, Tyr, Phe.

Accordingly, as used herein, the term "conservative substitutions" means an exchange of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt alpha-helices. Some preferred conservative substitutions within the above six groups are exchanges within the following sub-groups: (i) Ala, Val, Leu and Ile; (ii) Ser and Thr; (ii) Asn and Gln: (iv) Lys and Arg; and (v) Tyr and Phe. Given the known genetic code, and recombinant and synthetic DNA techniques, the skilled scientist readily can construct DNAs encoding the conservative amino acid variants.

As used herein, "non-conservative substitutions" or "non-conservative amino acid exchanges" are defined as exchanges of an amino acid by another amino acid listed in a different group of the six standard amino acid groups (1) to (6) as shown above. For ease of reference, the one-letter amino acid symbols recommended by the IUPAC-IUB Biochemical Nomenclature Commission are indicated as follows. The three letter codes are also provided for reference purposes.

| One Letter Code | Three Letter Code | Amino Acid Name |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Amino acid alterations such as amino acid substitutions may be introduced using known protocols of recombinant gene technology including PCR, gene cloning, site-directed mutagenesis of cDNA, transfection of host cells, and in vitro transcription which may be used to introduce such changes to the reference sequence resulting in an ADH enzyme variant. The enzyme variants can then be screened for ADH functional activity.

The alcohol dehydrogenase variant of the eighth aspect may, for example, have an amino acid sequence with at least about 70% or at least about 75% or at least about 80% or at least about 85% sequence identity to SEQ ID NO: 1. In particular embodiments, the alcohol dehydrogenase variant of the eighth aspect may have an amino acid sequence with at least about 90% or at least about 91% or at least about 92% or at least about 93% or at least about 94% or least about 95% or at least about 96% or at least about 97% or at least about 98% or at least about 99% sequence identity to SEQ ID NO: 1. The alcohol dehydrogenase of the eight aspect may, for example, have equal to or less than about 99% or equal to or less than about 98% sequence identity to SEQ ID NO: 1.

The alcohol dehydrogenase variant of the eighth aspect may, for example, exhibit up to about 60 amino acid alterations (e.g. substitutions, insertions, deletions, N-terminal truncations and/or C-terminal truncations) compared to SEQ ID NO: 1. For example, the alcohol dehydrogenase variant of the eighth aspect of the present invention may exhibit up to about 55 or up to about 50 or up to about 45 or up to about 40 or up to about 35 or up to about 30 or up to about 25 or up to about 20 or up to about 15 or up to about 10 or up to about 5 or up to about 4 or up to about 3 or up to about 2 or up to about 1 amino acid alterations compared to a reference amino acid sequence (e.g. compared to SEQ ID NO: 1). The amino acid exchanges may be conservative and/or non-conservative. The description of such exchanges above applies equally to the alcohol dehydrogenase variant of the eighth aspect.

The alcohol dehydrogenase variant of the eight aspect of the present invention is a variant of the amino acid sequence as set out in SEQ ID NO: 1. The alcohol dehydrogenase variant of the eight aspect of the present invention includes at least one amino acid alteration and/or have less than 100% sequence identity with SEQ ID NO: 1.

The alcohol dehydrogenase variant of the eight aspect of the present invention may include an amino acid alteration relative to one or more of the following amino acids in amino acid sequence as set out in SEQ ID NO: 1: R11, F30, V99, A100, L103, Q105, M106, L133, T145, N154, G161, V192, E194, K196, V198, Y209, M211, A213, E227 and S258. In these embodiments, the alcohol dehydrogenase variant of the eight aspect of the present invention may have an amino acid sequence with at least 90% identity with the amino acid sequence as set out in SEQ ID NO: 1.

The alteration relative to one or more of R11, F30, V99, A100, L103, Q105, M106, L133, T145, N154, G161, V192, E194, K196, V198, Y209, M211, A213, E227 and S258 in amino acid sequence as set out in SEQ ID NO: 1 may be a substitution. The alternation to R11 when present may be R11V. The alteration to F30 when present may be F30M or F30L. The alteration to V99 when present may be V99H. The alteration to A100 may be A100G. The alteration to L103 when present may be L1031 or L103M. The alteration to Q105 when present may be Q105T. The alteration to M106 when present may be M106T. The alteration to L133 when present may be L133M. The alteration to T145 when present may be T145N. The alteration to N154 when present may be N154V. The alteration to G161 when present may be G161T. The alteration to V192 when present may be V192Y. The alteration to E194 when present may be E194Q or E194K. The alteration to K196 when present may be K196N. The alteration to V198 when present may be V198L. The alteration to Y209 when present may be Y209G. The alteration to M211 when present may be M211P or M211R. The alteration to A213 when present may be A213G. The alteration to E227 when present may be E227Y. The alteration to S258 when present may be S258R.

The alcohol dehydrogenase variant of the eight aspect of the present invention may include an amino acid alteration relative to one or at least one, two or at least two of, or all three of T145, N154 and V198 in amino acid sequence as set out in SEQ ID NO: 1. In these embodiments, the alteration to T145 when present may be T145N. The alteration to N154 when present may be N154V. The alteration to V198 when present may be V198L. The alcohol dehydrogenase variant of the eight aspect of the present invention may include the alterations T145N, N154V and V198L relative to the amino acid sequence as set out in SEQ ID NO: 1.

The alcohol dehydrogenase variant of the eight aspect of the present invention may include an amino acid alteration relative to T145, N154, V192 and V198 in amino acid sequence as set out in SEQ ID NO: 1. In these embodiments, the alteration to T145 may be T145N; the alteration to N154 may be N154V; the alteration to V192 may be V192Y; and/or the alteration to V198 may be V198L. The alcohol dehydrogenase variant of the eight aspect of the present invention may include the alterations T145N, N154V, V192Y and V198L relative to the amino acid sequence as set out in SEQ ID NO: 1.

The alcohol dehydrogenase variant of the eight aspect of the present invention may include an amino acid alteration relative to A100, T145, N154, V192 and V198 in amino acid sequence as set out in SEQ ID NO: 1. In these embodiments, the alteration to A100 may be A100G; the alteration to T145 may be T145N; the alteration to N154 may be N154V; the alteration to V192 may be V192Y; and/or the alteration to V198 may be V198L. The alcohol dehydrogenase variant of the eight aspect of the present invention may include the alterations A100G, T145N, N154V, V192Y and V198L relative to the amino acid sequence as set out in SEQ ID NO: 1.

The alcohol dehydrogenase variant of the eight aspect of the present invention may include an amino acid alteration relative to A100, T145, N154, V192, V198 and one or both of K196 and S258 in amino acid sequence as set out in SEQ ID NO: 1. In these embodiments, the alteration to A100 may be A100G; the alteration to T145 may be T145N; the alteration to N154 may be N154V; the alteration to V192 may be V192Y; the alteration to K196 when present may be K196N; the alteration to V198 may be V198L; and/or the alteration in S258 when present may be S258R. The alcohol dehydrogenase variant of the eight aspect of the present invention may include the alterations A100G, T145N, N154V, V192Y, K196N, V198L and S258R relative to the amino acid sequence as set out in SEQ ID NO: 1.

The alcohol dehydrogenase variant of the eight aspect of the present invention may include an amino acid alteration relative to A100, T145, N154, V192, K196, V198, E227 and S258 in amino acid sequence as set out in SEQ ID NO: 1. In these embodiments, the alteration to A100 may be A100G; the alteration to T145 may be T145N; the alteration to N154 may be N154V; the alteration to V192 may be V192Y; the alteration to K196 may be K196N; the alteration to V198 may be V198L; the alteration to E227 may be E227T or E227Y; and/or the alteration in S258 may be S258R. The alcohol dehydrogenase variant of the eight aspect of the present invention may include the alterations A100G, T145N, N154V, V192Y, K196N, V198L, S258R and E227T or E227Y relative to the amino acid sequence as set out in SEQ ID NO: 1.

The alcohol dehydrogenase variant of the eight aspect of the present invention may include an amino acid alteration relative to A100, T145, N154, V192, K196, V198, E227, S258 and one, two or all of R11, F30 and A213 in amino acid sequence as set out in SEQ ID NO: 1. In these embodiments, the alternation to R11 when present may be R11V; the alteration to F30 when present may be F30M or F30L; the alteration to A100 may be A100G; the alteration to T145 may be T145N; the alteration to N154 may be N154V; the alteration to V192 may be V192Y; the alteration to K196 may be K196N; the alteration to V198 may be V198L; the alteration to A213 when present may be A213G; the alteration to E227 may be E227Y; and/or the alteration in S258 may be S258R. The alcohol dehydrogenase variant of the eight aspect of the present invention may include the alterations R11V, F30M or F30L, A100G, T145N, N154V, V192Y, K196N, V198L, A213G, S258R and E227Y relative to the amino acid sequence as set out in SEQ ID NO: 1.

The alcohol dehydrogenase variant of the eight aspect of the present invention may include an amino acid alteration relative to R11, F30, A100, T145, N154, V192, K196, V198, A213, E227, S258 and one, two, three or four of L103, E194, Y209 and M211 in amino acid sequence as set out in SEQ ID NO: 1. In these embodiments, the alternation to R11 may be R11V; the alteration to F30 may be F30M; the alteration to A100 may be A100G; the alteration to L103 when present may be L1031 or L103M; the alteration to T145 may be T145N; the alteration to N154 may be N154V; the alteration to V192 may be V192Y; the alteration to E194 when present may be E194Q or E194K; the alteration to K196 may be K196N; the alteration to V198 may be V198L; the alteration to Y209 when present may be Y209G; the alteration to M211 when present may be M211P or M211R; the alteration the alteration to A213 when present may be A213G; the alteration to E227 may be E227Y; and/or the alteration in S258 may be S258R. The alcohol dehydrogenase variant of the eight aspect of the present invention may include the alterations R11V, F30M, A100G, L1031 or L103M, T145N, N154V, V192Y, E194Q or E194K, K196N, V198L, A213G, Y209G, M211P or M211R, E227Y and S258R relative to the amino acid sequence as set out in SEQ ID NO: 1.

The alcohol dehydrogenase variant of the eight aspect of the present invention may include an amino acid alteration relative to R11, F30, A100, L103, T145, N154, V192, E194, K196, V198, Y209, M211, A213, E227 and S258 in amino acid sequence as set out in SEQ ID NO: 1. In these embodiments, the alternation to R11 may be R11V; the alteration to F30 may be F30M; the alteration to A100 may be A100G; the alteration to L103 when present may be L103M; the alteration to T145 may be T145N; the alteration to N154 may be N154V; the alteration to V192 may be V192Y; the alteration to E194 may be E194K; the alteration to K196 may be K196N; the alteration to V198 may be V198L; the alteration to Y209 may be Y209G; the alteration to M211 may be M211R; the alteration the alteration to A213 when present may be A213G; the alteration to E227 may be E227Y; and/or the alteration in S258 may be S258R. The alcohol dehydrogenase variant of the eight aspect of the present invention may include the alterations R11V, F30M, A100G, L103M, T145N, N154V, V192Y, E194K, K196N, V198L, A213G, Y209G, M211R, E227Y and S258R relative to the amino acid sequence as set out in SEQ ID NO: 1.

The alcohol dehydrogenase variant of the eight aspect of the present invention may additionally include an amino acid alteration relative to one or more of V99, Q105, M106, L133 and G161 in the amino acid sequence as set out in SEQ ID NO: 1. The alcohol dehydrogenase variant of the eight aspect of the present invention may additionally include an amino acid alteration relative to V99, M106, G161 and optionally L133 in amino acid sequence as set out in SEQ ID NO: 1. The alteration to V99 may be V99H; the alteration to M106 may be M106T; the alteration to L133 when present may be L133M; and the alteration to G161 may be G161T. The alteration to Q105 when present may be Q105T.

The alcohol dehydrogenase variant of the eighth aspect may, for example, have an amino acid sequence with at least about 70% or at least about 75% or at least about 80% or at least about 85% sequence identity with an amino acid sequence as set out in any one of SEQ ID NO: 2 to SEQ ID NO: 16. In particular embodiments, the alcohol dehydrogenase variant of the eighth aspect may have an amino acid sequence with at least about 90% or at least about 91% or at least about 92% or at least about 93% or at least about 94% sequence identity with an amino acid sequence as set out in any one of SEQ ID NO: 2 to SEQ ID NO: 16. The alcohol dehydrogenase variant of the eighth aspect may have an amino acid sequence having at least 95% or at least 96% or at least 97% or at least 98% or at least 99% identity with an amino acid sequence as set out in any one of SEQ ID NO: 2 to SEQ ID NO: 16. The alcohol dehydrogenase variant of the eighth aspect may have an amino acid sequence as set out in any one of SEQ ID NO: 2 to SEQ ID NO: 16. The alcohol dehydrogenase variant of the eighth aspect may have an amino acid sequence as set out in SEQ ID NO: 14, SEQ ID NO: 15 or SEQ ID NO: 16. The alcohol dehydrogenase variant of the eighth aspect may have an amino acid sequence as set out in SEQ ID NO: 15.

The alcohol dehydrogenase variant of the eight aspect of the present invention is particularly useful as the alcohol dehydrogenase of the bioconversion reaction of the present invention. The specific embodiments disclosed with respect to alcohol dehydrogenase variant of the eight aspect may be used as the alcohol dehydrogenase of the other aspects of the present invention.

The optimum conditions (e.g. pH and temperature) for the bioconversion reaction with alcohol dehydrogenase can be easily identified by a person of ordinary skill in the art.

For example, the optimum temperature for the alcohol dehydrogenase to be active may range from about 5° C. to about 50° C. For example, the optimum temperature for the alcohol dehydrogenase may be at least about 15° C. or at least about 20° C. or at least about 25° C. For example, the optimum temperature for the alcohol dehydrogenase may be up to about 45° C. or up to about 40° C. or up to about 35° C. For example, the optimum temperature for the alcohol dehydrogenase may range from about 15° C. to about 45° C. or from about 20° C. to about 40° C.

For example, the optimum pH for the alcohol dehydrogenase to be active may range from about 6 to about 9. For example, the optimum pH for the alcohol dehydrogenase may be at least about 7.0 or at least about 7.5. For example, the optimum pH for the alcohol dehydrogenase may be up to about 8.5 or up to about 8.0. For example, the optimum pH for the alcohol dehydrogenase may be from about 7.0 to about 8.5 or from about 7.5 to about 8.0.

The bioconversion reaction described herein may, for example, be carried out within 5° C. (+ or −5° C.) of the optimum temperature of the alcohol dehydrogenase enzyme. The bioconversion reaction described herein may, for example, be carried out within 0.5 (+ or −0.5) of the optimum pH of the alcohol dehydrogenase enzyme. The bioconversion reaction described herein may be carried out at the optimum temperature and/or the optimum pH of the alcohol dehydrogenase enzyme.

The bioconversion reaction described herein may, for example, take place in the presence of an enzyme cofactor and a cofactor regeneration system. An enzyme cofactor is a substance that increases the rate of the chemical reaction catalyzed by the enzyme. An enzyme cofactor regeneration system is a system that regenerates an enzyme cofactor.

The cofactor used with the alcohol dehydrogenase enzyme may, for example, be NADH, which generates $NAD^+$ when a ketone is converted to an alcohol, or NADPH, which generates $NADP^+$ when a ketone is converted to an alcohol.

The cofactor regeneration system may, for example, be enzyme coupled or substrate coupled. An example of an enzyme coupled cofactor regeneration system that could be used in the bioconversion reaction described herein is glucose and glucose dehydrogenase. Gluconate may be the by-product of this cofactor regeneration system.

A system may be required in order to maintain a pH in which the enzyme is active. An example of a substrate coupled cofactor regeneration system that could be used in the bioconversion reaction described herein is isopropanol. Acetone may be the by-product of this cofactor regeneration system.

The bioconversion reaction may, for example, take place in an aqueous solvent (e.g. including phosphate and/or other buffers).

The bioconversion reaction may, for example, take place in an organic/aqueous solvent mixture. The organic phase may, for example, be an alcohol such as isopropanol. The organic phase may, for example, be present in an amount up to about 40 vol %. The organic phase may be present in an amount in the range of about 5 vol % to about 40 vol %. The organic phase may be present in an amount in the range of about 15 vol % to about 35 vol %. The organic phase may be an alcohol, such as isopropanol, and present in an amount in the range of about 15 vol % to about 35 vol %. The organic phase may be an alcohol, such as isopropanol, and present in an amount in the range of about 15 vol % to about 35 vol % and the bioconversion reaction includes a variant alcohol dehydrogenase of the eight aspect of the present invention.

The alcohol dehydrogenase described herein may be encoded by a nucleic acid. The nucleic acid may, for example, be an isolated nucleic acid.

The nucleic acid sequence encoding an alcohol dehydrogenase as described herein may be comprised within a construct. As used herein, a "construct" is an artificially created segment of nucleic acid that is to be transfected into a target cell. The construct may comprise the nucleic acid encoding the alcohol dehydrogenase and an expression controller (e.g. promoter).

There is further provided herein a vector comprising a construct as described herein. As used herein, a "vector" is a DNA molecule that is used as a vehicle to artificially carry foreign genetic material into a cell where it can be replicated and/or expressed. The vector may, for example, be a plasmid, a viral vector, a cosmid, or an artificial chromosome. The terms "construct" and "vector" may overlap, for example where the construct is a plasmid.

In particular, the nucleic acid may encode an amino acid sequence described herein.

The term "nucleic acid" or "nucleic acid molecule" as used herein shall specifically refer to polynucleotides which can be DNA, cDNA, genomic DNA, synthetic DNA, or RNA, and can be double-stranded or single-stranded, the sense and/or an antisense strand. The term "nucleic acid" or "nucleic acid molecule" may particularly apply to polynucleotide(s), e.g. as full-length nucleotide sequence or fragments or parts thereof, which encode a polypeptide with enzymatic activity, e.g. an enzyme of a metabolic pathway, or fragments or parts thereof, respectively.

The term also includes a separate molecule such as a cDNA where the corresponding genomic DNA has introns and therefore a different sequence; a genomic fragment that lacks at least one of the flanking genes; a fragment of cDNA or genomic DNA produced by polymerase chain reaction (PCR) and that lacks at least one of the flanking genes; a restriction fragment that lacks at least one of the flanking genes; a DNA encoding a non-naturally occurring protein such as a fusion protein (e.g. a His tag), mutein, or fragment of a given protein; and a nucleic acid which is a degenerate variant of a cDNA or a naturally occurring nucleic acid. In addition, it includes a recombinant nucleotide sequence that is part of a hybrid gene, i.e. a gene encoding a non-naturally occurring fusion protein. Fusion proteins can add one or more amino acids (such as but not limited to Histidine (His)) to a protein, usually at the N-terminus of the protein but also at the C-terminus or fused within regions of the protein. Such fusion proteins or fusion vectors encoding such proteins typically serve three purposes: (i) to increase production of recombinant proteins; (ii) to increase the solubility of the recombinant protein; and (iii) to aid in the purification of the recombinant protein by providing a ligand for affinity purification.

The term "nucleic acid" or "nucleic acid molecule" also includes codon optimised sequences suitable for expression in a particular microbial host cell (e.g. *E. coli* host cell). As used herein, the term "codon optimized" means a nucleic acid protein coding sequence which has been adapted for expression in a prokaryotic or a eukaryotic host cell, particularly bacterial host cells such as *E. coli* host cells by substitution of one or more or preferably a significant number of codons with codons that are more frequently used in bacterial (e.g. *E. coli*) host cell genes.

In this regard, the nucleotide sequence encoding the amino acid sequence of an alcohol dehydrogenase enzyme may be the original one as found in the source or the gene can be codon-optimized for the selected host organisms, such as e.g. *E. coli*.

A ribonucleic acid (RNA) molecule can be produced by in vitro transcription. Segments of DNA molecules are also considered within the scope of the disclosure, and can be produced by, for example, the polymerase chain reaction (PCR) or generated by treatment with one or more restriction endonucleases. Segments of a nucleic acid molecule may be referred to as DNA fragments of a gene, in particular those that are partial genes. A fragment can also contain several open reading frames (ORF), either repeats of the same ORF or different ORF's. The term shall specifically refer to coding nucleotide sequences, but shall also include nucleotide sequences which are non-coding, e.g. untranscribed or untranslated sequences, or encoding polypeptides, in whole or in part. The genes as used herein, e.g. for assembly, diversification or recombination can be non-coding sequences or sequences encoding polypeptides or protein encoding sequences or parts or fragments thereof having sufficient sequence length for successful recombination events. More specifically, said genes have a minimum length of 3 bp, preferably at least 100 bp, more preferred at least 300 bp. It will be apparent from the foregoing that a reference to an isolated DNA does not mean a DNA present among hundreds to millions of other DNA molecules within, for example, cDNA or genomic DNA libraries or genomic DNA restriction digests in, for example, a restriction digest reaction mixture or an electrophoretic gel slice. An isolated nucleic acid molecule of the present disclosure encompasses segments that are not found as such in the natural state.

As used herein, the term "isolated DNA" can refer to (1) a DNA that contains sequence not identical to that of any naturally occurring sequence, a polynucleotide or nucleic acid which is not naturally occurring, (e.g. is made by the artificial combination (e.g. artificial manipulation of isolated segments of nucleic acids, e.g. by genetic engineering techniques) of two otherwise separated segments of sequences through human intervention) or (2), in the context of a DNA with a naturally-occurring sequence (e.g. a cDNA or genomic DNA), a DNA free of at least one of the genes that flank the gene containing the DNA of interest in the genome of the organism in which the gene containing the DNA of interest naturally occurs.

The term "isolated DNA" as used herein, specifically with respect to nucleic acid sequences may also refer to nucleic acids or polynucleotides produced by recombinant DNA techniques, e.g. a DNA construct comprising a polynucleotide heterologous to a host cell, which is optionally incorporated into the host cell. A chimeric nucleotide sequence may specifically be produced as a recombinant molecule. The term "recombination" shall specifically apply to assembly of polynucleotides, joining together such polynucleotides or parts thereof, with or without recombination to achieve a cross-over or a gene mosaic. For example, it is performed to join together nucleic acid segments of desired functions to generate a desired combination of functions. A recombinant gene encoding a polypeptide described herein may include the coding sequence for that polypeptide, operably linked, in sense orientation, to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence.

The term "recombinant" as used herein, specifically with respect to enzymes shall refer to enzymes produced by recombinant DNA techniques, i.e. produced from cells transformed by an exogenous DNA construct encoding the desired enzyme. "Synthetic" enzymes are those prepared by chemical synthesis. A chimeric enzyme may specifically be produced as recombinant molecule. The term "recombinant DNA" therefore includes a recombinant DNA incorporated into a vector into an autonomously replicating plasmid or virus, or into the genomic DNA of a prokaryote or eukaryote (or the genome of a homologous cell, at a position other than the natural chromosomal location).

In a further aspect the nucleic acid molecule(s) of the present disclosure is/are operatively linked to expression control sequences allowing expression in prokaryotic and/or eukaryotic host cells. As used herein, "operatively linked" means incorporated into a genetic construct so that expression control sequences effectively control expression of a coding sequence of interest. The transcriptional/translational regulatory elements referred to above include but are not limited to inducible and non-inducible, constitutive, cell cycle regulated, metabolically regulated promoters, enhancers, operators, silencers, repressors and other elements that are known to those skilled in the art and that drive or otherwise regulate gene expression. Such regulatory elements include but are not limited to regulatory elements directing constitutive expression or which allow inducible expression like, for example, CUP-1 promoter, the tet-repressor as employed, for example, in the tet-on or tet-off systems, the lac system, the trp system regulatory elements. By way of example, Isopropyl β-D-I-thiogalactopyranoside (IPTG) is an effective inducer of gene expression in the concentration range of 100 μM to 1.0 mM. This compound is a molecular mimic of allolactose, a lactose metabolite that triggers transcription of the lac operon, and it is therefore used to induce gene expression when the gene is under the control of the lac operator. Another example of a regulatory element which induces gene expression is lactose. Similarly, the nucleic acid molecule(s) of the present disclosure can form part of a hybrid gene encoding additional polypeptide sequences, for example, a sequence that functions as a marker or reporter. Examples of marker and reporter genes including beta-lactamase, chloramphenicol acetyltransferase (CAT), adenosine deaminase (ADA), aminoglycoside phosphotransferase dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). As with many of the standard procedures associated with the practice of the disclosure, skilled artisans will be aware of additional useful reagents, for example, additional sequences that can serve the function of a marker or reporter.

There is also provided herein a recombinant polynucleotide encoding the alcohol dehydrogenase enzyme, which may be inserted into a vector for expression and optional purification. One type of vector is a plasmid representing a circular double stranded DNA loop into which additional DNA segments are ligated. Certain vectors can control the expression of genes to which they are functionally linked. These vectors are called "expression vectors". Usually expression vectors suitable for DNA recombination techniques are of the plasmid type. Typically, an expression vector comprises a gene such as the alcohol dehydrogenase as described herein. In the present description, the terms "plasmid" and "vector" may be used interchangeably since the plasmid is the vector type most often used.

Such vectors can include DNA sequences which include but are not limited to DNA sequences that are not naturally present in the host cell, DNA sequences that are not normally transcribed into RNA or translated into a protein ("expressed") and other genes or DNA sequences which one desires to introduce into the non-recombinant host. It will be appreciated that typically the genome of a recombinant host described herein is augmented through the stable introduction of one or more recombinant genes. However, autonomous or replicative plasmids or vectors can also be used within the scope of this disclosure. Moreover, the present disclosure can be practiced using a low copy number, e.g. a single copy, or high copy number (as exemplified herein) plasmid or vector.

The vector of the present disclosure includes plasmids, phagemids, phages, cosmids, artificial bacterial and artificial yeast chromosomes, knock-out or knock-in constructs, synthetic nucleic acid sequences or cassettes and subsets may be produced in the form of linear polynucleotides, plasmids, megaplasmids, synthetic or artificial chromosomes, such as plant, bacterial, mammalian or yeast artificial chromosomes.

It is preferred that the proteins encoded by the introduced polynucleotide are expressed within the cell upon introduction of the vector. The diverse gene substrates may be incorporated into plasmids. The plasmids are often standard cloning vectors, e.g. bacterial multicopy plasmids. The substrates can be incorporated into the same or different plasmids. Often at least two different types of plasmid having different types of selectable markers are used to allow selection for cells containing at least two types of vectors.

Typically bacterial or yeast cells may be transformed with any one or more nucleotide sequences as is well known in the art. For in vivo recombination, the gene to be recombined with the genome or other genes is used to transform the host using standard transforming techniques. In a suitable embodiment DNA providing an origin of replication is included in the construct. The origin of replication may be suitably selected by the skilled person. Depending on the nature of the genes, a supplemental origin of replication may not be required if sequences are already present with the genes or genome that are operable as origins of replication themselves.

Recombinant host cells may be used in the bioconversion methods described herein. Alternatively, isolated alcohol dehydrogenase enzymes may be used in the bioconversion methods described herein.

There is further provided herein a recombinant host cell comprising a nucleic acid sequence or a construct or a vector as described herein. There is further provided herein a recombinant host cell that produces an alcohol dehydrogenase enzyme as described herein.

The bioconversion processes described herein for producing one or more of a compound of formula (II), a compound of formula (III), and a compound of formula (IV) may, for example, comprise culturing a recombinant host cell as described herein. As used herein, the term "culturing" refers to a process of maintaining living cells such that they produce an alcohol dehydrogenase enzyme as described herein that can be used in a bioconversion process for producing one or more of a compound of formula (II), a compound of formula (III), and a compound of formula (IV) as described herein. It is not necessary for the cells to divide and replicate themselves, although this is not excluded.

A bacterial or yeast cell may be transformed by exogenous or heterologous DNA when such DNA has been introduced inside the cell. The transforming DNA may or may not be integrated, i.e. covalently linked into the genome of the cell. In prokaryotes, and yeast, for example, the transforming DNA may be maintained on an episomal element such as a plasmid. With respect to eukaryotic cells, a stably transfected cell is one in which the transfected DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

Generally, the introduced DNA is not originally resident in the host that is the recipient of the DNA, but it is within the scope of the disclosure to isolate a DNA segment from a given host, and to subsequently introduce one or more additional copies of that DNA into the same host, e.g. to enhance production of the product of a gene or alter the expression pattern of a gene. In some instances, the introduced DNA will modify or even replace an endogenous gene or DNA sequence, e.g. by homologous recombination or site-directed mutagenesis. Suitable recombinant hosts include microorganisms, plant cells, and plants.

The present disclosure also features recombinant hosts. The term "recombinant host", also referred to as a "genetically modified host cell" or a "transgenic cell" denotes a host cell that comprises a heterologous nucleic acid or the genome of which has been augmented by at least one incorporated DNA sequence. A host cell of the present disclosure may be genetically engineered with the polynucleotide or the vector as outlined above.

The host cells that may be used for purposes of the disclosure include but are not limited to prokaryotic cells such as bacteria (for example, *E. coli* and *B. subtilis*), which may, for example, be transformed with, for example, recombinant bacteriophage DNA, plasmid DNA, bacterial artificial chromosome, or cosmid DNA expression vectors containing the polynucleotide molecules of the disclosure; simple eukaryotic cells like yeast (for example, *Saccharomyces* and *Pichia*), which may, for example, be transformed with, for example, recombinant yeast expression vectors containing the polynucleotide molecule of the disclosure. Depending on the host cell and the respective vector used to introduce the polynucleotide of the disclosure the polynucleotide can integrate, for example, into the chromosome or the mitochondrial DNA or can be maintained extrachromosomally like, for example, episomally or can be only transiently comprised in the cells.

The term "cell" as used herein in particular with reference to genetic engineering and introducing one or more genes or an assembled cluster of genes into a cell, or a production cell is understood to refer to any prokaryotic or eukaryotic cell. Prokaryotic and eukaryotic host cells are both contemplated for use according to the disclosure, including bacterial host cells like *E. coli* or *Bacillus* sp, yeast host cells, such as *S. cerevisiae*, insect host cells, such as *Spodoptora frugiperda* or human host cells, such as HeLa and Jurkat.

Specifically, the cell is a eukaryotic cell, preferably a fungal, mammalian or plant cell, or a prokaryotic cell. Suitable eukaryotic cells include, for example, without limitation, mammalian cells, yeast cells, or insect cells (including Sf9), amphibian cells (including melanophore cells), or worm cells including cells of *Caenorhabditis* (including *Caenorhabditis elegans*). Suitable mammalian cells include, for example, without limitation, COS cells (including Cos-1 and Cos-7), CHO cells, HEK293 cells, HEK293T cells, HEK293 T-Rex™ cells, or other transfectable eucaryotic cell lines. Suitable bacterial cells include without limitation *E. coli.*

Preferably prokaryotes, such as *E. coli, Bacillus, Streptomyces*, or mammalian cells, like Hela cells or Jurkat cells, or plant cells, like *Arabidopsis*, may be used.

The cell may, for example, be selected from prokaryotic, yeast, plant, and/or insect host cells.

The cell may be an *Aspergillus* sp. or a fungal cell, for example, it can be selected from the group consisting of the genera *Saccharomyces, Candida, Kluyveromyces, Hansenula, Schizosaccharomyces, Yarrowia, Pichia* and *Aspergillus.*

The cell may be a bacteria cell, for example, having a genus selected from *Escherichia, Streptomyces, Bacillus, Pseudomonas, Lactobacillus* and *Lactococcus*. For example, the bacteria may be *E. coli.*

The *E. coli* host cell may be an *E. coli* host cell which is recognized by the industry and regulatory authorities (including but not limited to an *E. coli* K12 host cell or an *E. coli* BL21 host cell).

One host cell to use with the present disclosure is *E. coli*, which may be recombinantly prepared as described herein. Thus, the recombinant host may be a recombinant *E. coli* host cell. There are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

In one embodiment, the recombinant *E. coli* microorganism comprises nucleotide sequences encoding alcohol dehydrogenase enzyme genes.

The recombinant *E. coli* microorganism may comprise a vector construct as described herein. In another embodiment, the recombinant *E. coli* microorganism comprises nucleotide sequences encoding the alcohol dehydrogenase enzymes disclosed herein.

Another host cell suitable for use with the present disclosure is *S. cerevisiae* which is a widely used chassis organism in synthetic biology. Thus, the recombinant host may be *S. cerevisiae*. There are libraries of mutants, plasmids, detailed computer models of metabolism and other information available for *S. cerevisiae*, allowing for rational design of various modules to enhance product yield. Methods are known for making recombinant *S. cerevisiae* microorganisms.

Culturing of cells may be performed in a conventional manner. The culture medium may contain a carbon source, at least one nitrogen source and inorganic salts, and vitamins may be added to it. The constituents of this medium can be the ones which are conventionally used for culturing the species of microorganism in question. Carbon sources of use in the instant method include any molecule that can be metabolized by the recombinant host cell to facilitate growth and/or production of the one or more of a compound of formula (II), a compound of formula (III), and a compound of formula (IV). Examples of suitable carbon sources include, but are not limited to, sucrose (e.g. as found in molasses), fructose, xylose, glycerol, glucose, cellulose, starch, cellobiose or other glucose containing polymer.

In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g. protein, and then provided with a source of carbon only during the fed-batch phase.

The suitability of a recombinant host cell microorganism for use in the methods of the present disclosure may be determined by simple test procedures using well known methods. For example, the microorganism to be tested may be propagated in a rich medium (e.g. LB-medium, Bacto-tryptone yeast extract medium, nutrient medium and the like) at a pH, temperature and under reaction conditions commonly used for propagation of the microorganism. Once recombinant microorganisms (i.e. recombinant host cells) are selected that produce the desired products, the products are typically produced by a production host cell line on the large scale by suitable expression systems and fermentations, e.g. by microbial production in cell culture.

The recombinant microorganism may be grown in a batch, fed batch or continuous process or combinations thereof. Typically, the recombinant microorganism is grown in a fermenter at a defined temperature(s) in the presence of a suitable nutrient source, e.g. a carbon source, for a desired period of time to produce sufficient enzyme to convert the compound of formula (I) to one or more of a compound of formula (II), a compound of formula (III), and a compound of formula (IV). The recombinant host cells may be cultivated in any suitable manner, for example by batch cultivation or fed-batch cultivation.

As used herein, the term "batch cultivation" is a cultivation method in which culture medium is neither added nor withdrawn during the cultivation.

As used herein, the term "fed-batch" means a cultivation method in which culture medium is added during the cultivation but no culture medium is withdrawn.

One embodiment of the present disclosure provides a method of making one or more of a compound of formula (II), a compound of formula (III), and a compound of formula (IV) in a cellular system comprising expressing alcohol dehydrogenase enzyme under suitable conditions in a cellular system, feeding a compound of formula (I) to the cellular system, converting the compound of formula (I) to the one or more of a compound of formula (II), a compound of formula (III), and a compound of formula (IV), using the alcohol dehydrogenase produced using the cellular system, collecting the one or more of a compound of formula (II), a compound of formula (III), and a compound of formula (IV) from cellular system and optionally isolating from the system. Expression of other nucleotide sequences may serve to enhance the method. The method can include the additional expression of other nucleotide sequences in the cellular system. The expression of other nucleotide sequences may enhance the bioconversion pathway for making the one or more of a compound of formula (II), a compound of formula (III), and a compound of formula (IV). A further embodiment of the present disclosure is a method of making one or more of a compound of formula (II), a compound of formula (III), and a compound of formula (IV), comprising growing host cells comprising alcohol dehydrogenase genes, producing alcohol dehydrogenase in the host cells, feeding a compound of formula (I) to the host cells, incubating the host cells under conditions of pH, temperature and solubilizing agent suitable to promote the conversion of the compound of formula (I) to the one or more of the compound of formula (II), the compound of formula (III), and the compound of formula (IV), and collecting the one or more of the compound of formula (II), the compound of formula (III), and the compound of formula (IV). The production of the alcohol dehydrogenase in the host cells provides a method of making the one or more of the compound of formula (II), the compound of formula (III), and the compound of formula (IV) when the compound of formula (I) is added to the host cells under suitable reaction conditions.

The recombinant host cell microorganism may be cultured in a number of ways in order to provide cells in suitable amounts expressing the alcohol dehydrogenase for the subsequent bioconversion step. Since the microorganisms applicable for the bioconversion step vary broadly (e.g. yeasts, bacteria and fungi), culturing conditions are, of course, adjusted to the specific requirements of each species and these conditions are well known and documented. Any of the art known methods for growing cells of recombinant host cell microorganisms may be used to produce the cells utilizable in the subsequent bioconversion step of the present disclosure. Typically the cells are grown to a particular density (measurable as optical density (OD)) to produce a sufficient biomass for the bioconversion reaction.

The cultivation conditions chosen influence not only the amount of cells obtained (the biomass) but the quality of the cultivation conditions also influences how the biomass becomes a biocatalyst. The recombinant host cell microorganism expressing the alcohol dehydrogenase gene and producing the alcohol dehydrogenase enzyme is termed a biocatalyst which is suitable for use in a bioconversion reaction. In some embodiments the biocatalyst is a recombinant whole cell producing alcohol dehydrogenase enzyme or it may be in suspension or an immobilized format. In other embodiments, the biocatalyst is a membrane fraction or a liquid fraction prepared from the recombinant whole cell producing the alcohol dehydrogenase. The recombinant whole cells producing alcohol dehydrogenase include whole cells collected from the fermenter (for the bioconversion reaction) or the cells in the fermenter (which are then used in a one-pot reaction). The recombinant whole cell producing alcohol dehydrogenase can include intact recombinant whole cell and/or cell debris. Either way, the alcohol dehydrogenase may be associated with a membrane (such as a cell membrane) in some way in order to receive and/or interact with a substrate (e.g. compound of formula (I)), which membrane (such as a cell membrane) can be part of or comprise a whole cell (e.g. a recombinant whole cell). The alcohol dehydrogenase may also be in an immobilized form (e.g. associated with an enzyme carrier) which allows the alcohol dehydrogenase to interact with a substrate (e.g. compound of formula (I)). The alcohol dehydrogenase enzyme may also be used in a soluble form (including cell-free extracts).

In one embodiment, the biocatalyst is produced in sufficient amounts (to create a sufficient biomass), harvested and washed (and optionally stored (e.g. frozen or lyophilized)) before the bioconversion step.

In a further embodiment, the cells are produced in sufficient amounts (to create a sufficient biocatalyst) and the reaction conditions are then adjusted without the need to harvest and wash the biocatalyst for the bioconversion reaction. This one step (or "one pot") method is advantageous as it simplifies the process while reducing costs. The culture medium used to grow the cells may also be suitable for use in the bioconversion reaction provided that the reaction conditions are adjusted to facilitate the bioconversion reaction.

The alcohol dehydrogenase used in the presently described methods may, for example, be used as an isolated enzyme (i.e. free enzyme). For example, the alcohol dehydrogenase used in the presently described methods may be in a lyophilized cell-free extract. Thus, the methods described herein may comprise contacting a compound of formula (I) with an isolated alcohol dehydrogenase.

Alternatively, the alcohol dehydrogenase used in the presently described methods may be expressed from whole cells (e.g. recombinant cells). Thus, the methods described herein may, for example, take place in the presence of whole cells.

To obtain an isolated enzyme, the recombinant whole-cell may be lysed (i.e. destruction of the cell membrane) by means of e.g. treatment with enzymes (lysozyme), detergents or solutions of high salt concentration, homogenization, ultra-sonication, or by means of the freeze-thaw method. The cell debris may be removed by e.g. centrifugation or filtration to obtain the cell-free extract. The cell-free extract may then be lyophilized. Alternatively, the cell-free extract may be objected to further purification by e.g. size-exclusion chromatography (gel filtration), affinity chromatography, ion exchange chromatography, differential denaturation by heat treatment or precipitation (e.g. by acetone or ammonium sulphate). At any step, the purification may be stopped to obtain enzyme formulations at different grades suitable to be used for the biotransformation.

Whilst the terms "mixture" or "reaction mixture" may be used interchangeably with the term "medium" in the present disclosure (especially as it relates to a "one pot" reaction), it should be noted that growing the cells to create a sufficient biomass requires a cell culture/fermentation medium but a medium is not required for the bioconversion reaction as a reaction buffer/solvent will suffice at a suitable pH.

The bioconversion methods of the present disclosure are carried out under conditions of time, temperature, pH and solubilizing agent to provide for conversion of the compound of formula (I) to the one or more of a compound of formula (II), a compound of formula (III), and a compound of formula (IV).

It may be useful to include a solubilizing agent (e.g. a surfactant, detergent, solubility enhancer, water miscible organic solvent and the like) in the bioconversion reaction.

As used herein, the term "surfactant" means a component that lowers the surface tension (or interfacial tension) between two liquids or between a liquid and a solid. Surfactants may act as detergents, wetting agents, emulsifiers, foaming agents, and dispersants. Examples of surfactants include but are not limited to Triton X-100, Tween 80, taurodeoxycholate, Sodium taurodeoxycholate, Sodium dodecyl sulfate (SDS), and/or sodium lauryl sulfate (SLS).

In some embodiments, the one or more of a compound of formula (II), a compound of formula (III), and a compound of formula (IV) is produced using a biocatalyst to which the compound of formula (I) substrate is added.

It is possible to add the substrate by feeding using known means (e.g. peristaltic pump, infusion syringe and the like).

A fermenter may be used to grow recombinant host cells expressing the alcohol dehydrogenase gene and producing active alcohol dehydrogenase enzyme to a sufficient biomass concentration suitable for use as a biocatalyst in the same fermenter vessel which may be used to convert the compound of formula (I) source to the one or more of a compound of formula (II), a compound of formula (III), and a compound of formula (IV).

The initial concentration of compound (I) (as substrate) in the bioconversion reaction may be about 10 mM or greater, about 20 mM or greater or about 30 mM or greater. For example, the initial concentration of compound (I) (as substrate) in the bioconversion reaction may be about 40 mM. In certain embodiments, the initial concentration of compound (I) (as substrate) in the bioconversion reaction may be about 50 mM or greater, about 100 mM or greater, about 150 mM or greater, about 200 mM or greater, about 250 mM or greater, about 300 mM or greater or about 400 mM or greater. For example, the initial concentration of compound (I) (as substrate) in the bioconversion reaction may be about 600 mM. For example, the initial concentration of compound (I) (as substrate) in the bioconversion reaction may be in the range between about 600 mM and about 1 M. The initial concentration of compound (I) (as substrate) in the bioconversion reaction may be about 50 mM or greater, about 100 mM or greater, about 150 mM or greater, about 200 mM or greater, about 250 mM or greater, about 300 mM or greater, or about 400 mM or greater, or about 600 mM or greater, or about 800 mM or greater, or about 1 M, and the alcohol dehydrogenase is the variant alcohol dehydrogenase of the eighth aspect of the present invention.

The initial alcohol dehydrogenase concentration in the bioconversion reaction may be about 25 g/L or lower, about 20 g/L or lower, about 18 g/L or lower, about 16 g/L or lower, about 14 g/L or lower, about 12 g/L or lower or about 10 g/L or lower. In certain embodiments, the initial alcohol dehydrogenase concentration in the bioconversion reaction may be about 10 g/L or lower, about 9 g/L or lower, about 8 g/L or lower, about 7 g/L or lower, about 6 g/L or lower, about 5 g/L or lower, about 4 g/L or lower, about 3 g/L or about 2 g/L or lower. The initial alcohol dehydrogenase concentration in the bioconversion reaction may be about 10 g/L or lower, about 9 g/L or lower, about 8 g/L or lower, about 7 g/L or lower, about 6 g/L or lower, about 5 g/L or lower, about 4 g/L or lower, about 3 g/L or about 2 g/L or lower and the alcohol dehydrogenase is the variant alcohol dehydrogenase of the eighth aspect of the present invention.

The activity of the alcohol dehydrogenase enzyme may be defined via the % conversion (amount of product/(amount of product+amount of remaining starting material))×100) in mol percent. Preferably, the % conversion of the compound of formula (I) into one or more of a compound of formula (II), a compound of formula (III), and a compound of formula (IV) in the presence of an alcohol dehydrogenase enzyme produces a compound of formula (II), a compound of formula (III), and a compound of formula (IV) in at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, given in mol percent and based on the mols of compound of formula (I) employed; especially preferably, the % conversion is between 50 and 100, 60 and 100, 70 and 100, 80 and 100, or 90 and 100 mol %.

In a preferred embodiment of the invention, the % conversion is determined over a defined time period of, for example, 4, 6, 8, 10, 12, 16, 20, 24, 36 or 48 hours, during which compound of formula (I) is converted into one or more of a compound of formula (II), a compound of formula (III), and a compound of formula (IV) by an alcohol dehydrogenase enzyme.

Preferably, after the bioconversion reaction has taken place, the bioconversion reaction mixture is extracted (e.g. using an organic solvent such as methyl tert-butyl ether (MTBE)), the enzyme or biomass is removed from the reaction mixture (e.g. by centrifugation or by filtration, for example filtration using diatomaceous earth such as Celite), and then dried (e.g. using magnesium sulphate) prior to any treatment with acid. Any solvent may, for example, be evaporated.

Second Step—Treatment with Acid

An acid treatment step may follow the bioconversion reaction in order to provide one or more compound(s) of formula (v) by dehydration and/or rearrangement of the compound of formula (II), the compound of formula (III) and/or the compound of formula (IV), Formula (V)

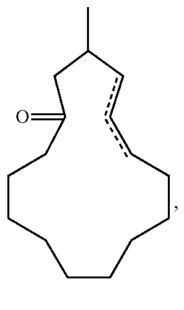

wherein one of ------ is a single bond and the other is a double bond.

Thus, the methods described herein may, for example, further comprise treating the one or more of a compound of formula (II), a compound of formula (III), and a compound of formula (IV) with acid to provide one or more compound(s) of formula (V). The methods described herein may further comprise treating a mixture comprising a compound of formula (II), a compound of formula (III), and a compound of formula (IV) with acid to provide one or more compound(s) of formula (V).

The methods described herein may, for example, further comprise treating the one or more of a compound of formula (II), a compound of formula (III), and a compound of formula (IV) with acid to provide one or more of a compound of formula (Va), a compound of formula (Vb), a compound of formula (Vc), and a compound of formula (Vd), Formula (Va)

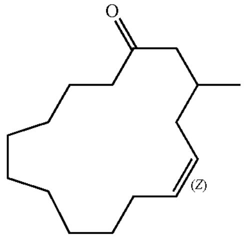

Formula (Vb)

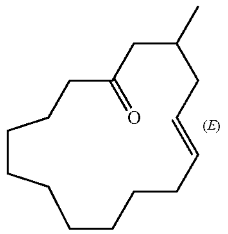

Formula (Vc)

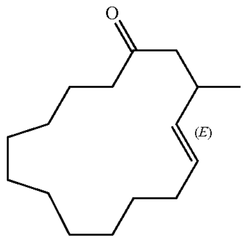

Formula (Vd)

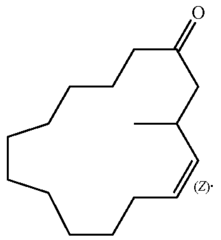

The methods described herein may, for example, further comprise treating a mixture comprising a compound of formula (II), a compound of formula (III), and a compound of formula (IV) with acid to provide a mixture comprising one or more of a compound of formula (Va), a compound of formula (Vb), a compound of formula (Vc), and a compound of formula (Vd)

The treatment with acid may, for example, provide two, three or four of a compound of formula (Va), a compound of formula (Vb), a compound of formula (Vc), and a compound of formula (Vd). The treatment with acid may, for example, provide one, two or three of a compound of formula (Va), a compound of formula (Vb), and a compound of formula (Vc). A compound of formula (Vd) may or may not be provided.

For example, the treatment with acid may provide a mixture comprising a compound of formula (Va), a compound of formula (Vb), and a compound of formula (Vc). The mixture may, for example, further comprise a compound of formula (Vd). Alternatively, the mixture may not comprise a compound of formula (Vd).

The methods described herein may, for example, further comprise treating a mixture comprising a compound of formula (II), a compound of formula (III) and a compound of formula (IV) with acid to provide a mixture comprising a compound of formula (Va), a compound of formula (Vb) and a compound of formula (Vc). The mixture may, for example, further comprise a compound of formula (Vd). Alternatively, the mixture may not comprise a compound of formula (Vd).

The relative amounts of the compounds of formula (V) and their enantiomers may, for example, be as described herein in relation to the compositions of the present disclosure.

Any suitable conditions for the treatment with acid step may be used.

In principle, any acid (compound having Lewis or Brønsted acidity) can be used.

The acid may, for example, be a strong acid. By strong acid, it is meant an acid that completely dissociates in aqueous solution. Strong and weak acids may be identified by determining $pK_a$ value. The $pK_a$ value of an acid (HA) which dissociates into ions ($A^-$ and $H^+$) in aqueous solution may be determined using the following equations.

$$pk_a = -\log_{10} K_a$$

$$K_a = [A-][H+]/[HA]$$

Acids having a $pK_a$ value of less than 0 in aqueous solution are considered to be strong acids. Acids having a $pK_a$ value of 0 or more in aqueous solution are considered to be weak acids.

Examples of suitable acids include, for example, sulphuric acid, sulphonic acids (e.g. para-toluene sulphonic acid (pTSA) or methanesulphonic acid), phosphoric acid, hydrochloric acid, nitric acid, hydrobromic acid, perchloric acid, hydroiodic acid, benzoic acid, Montmorillonite K10 (clay), and Lewis acids (such as iron (III) chloride, aluminium (III) chloride, $BF_3$*$Et_2O$, titanium (IV) chloride, zinc (II) chloride, tin (IV) chloride).

The acid used, temperature of the reaction, and/or reaction time for the treatment with acid can be selected depending on the desired products.

The treatment with acid may, for example, be carried out at a temperature ranging from about 40° C. to about 100° C. For example, the treatment with acid may be carried out at a temperature of at least about 55° C. or at least about 60° C. or at least about 65° C. or at least about 70° C. For example, the treatment with acid may be carried out at a temperature up to about 100° C. or up to about 95° C. or up to about 90° C. For example, the treatment with acid may be carried out at a temperature ranging from about 60° C. to about 100° C. or from about 70° C. to about 100° C. The temperature may, for example, achieve acid reflux.

The treatment with acid may, for example, be carried out for a period of time ranging from about 1 hour to about 70 hours. For example, the treatment with acid may be carried out for a period of time of at least about 4 hours or at least about 6 hours or at least about 8 hours. For example, the treatment with acid may be carried out for a period of time up to about 60 hours or up to about 50 hours or up to about 40 hours or up to about 30 hours or up to about 20 hours or up to about 18 hours or up to about 16 hours or up to about 14 hours. For example, the treatment with acid may be carried out for a period of time ranging from 4 hours to 50 hours or from 4 hours to 30 hours or from 4 hours to 20 hours or from 4 hours to 18 hours or from 6 hours to about 16 hours.

For example, certain reaction conditions such as the use of certain acids may promote the formation of a compound of formula (Vd). For example, using phosphoric acid may promote the formation of a compound of formula (Vd). Using pTSA may not promote the formation of a compound of formula (Vd).

For example, stronger acids, higher temperatures, and/or longer reaction times may promote a double bond shift resulting in the formation of a compound of formula (VIa) and/or a compound of formula (VIb), Formula (VIa)

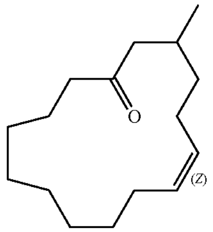

Formula (VIb)

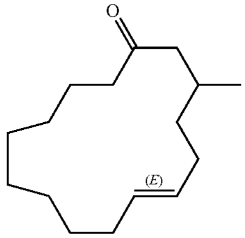

.

The methods described herein may, for example, provide a compound of formula (VIa) and/or a compound of formula (VIb). Alternatively, the methods described herein may not provide a compound of formula (VIa) and/or a compound of formula (VIb). Thus, the reaction conditions may be selected in order to avoid the formation of a compound of formula (VIa) and/or a compound of formula (VIb).

Further Method Steps

The one or more compound(s) of formula (V) may be purified, for example by distillation or chromatography, to remove any starting material, intermediate compound(s) (e.g. one or more of a compound of formula (II), a compound of formula (III) and a compound of formula (IV)), byproducts and/or further impurities.

For example, the reaction mixture from the acid treatment step may be extracted (e.g. using an organic solvent such as MTBE) and dried (e.g. using magnesium sulfate). Any solvent may, for example, be evaporated.

The methods described herein may, for example, further comprise an enrichment distillation step after the treatment with acid to obtain a desired stereoisomer ratio. The desired stereoisomer ratio may, for example, depend on the intended use of the product (the one or more compound(s) of formula (V)).

An enrichment distillation is a distillation in which the proportion of a desired stereoisomer is increased. Distillation may, for example, take place via bulb-to-bulb distillation, fractional distillation or vacuum distillation.

Compositions Obtained by the Disclosed Methods

There is further provided herein the compositions obtained by and/or obtainable by the methods disclosed herein.

There is provided herein a composition comprising a compound of formula (II), a compound of formula (III), and a compound of formula (IV). These compositions may, for example, be obtained by and/or obtainable by the bioconversion reaction described herein.

There is provided herein a composition comprising one or more compounds of formula (V). For example, there is provided herein a composition comprising one or more of a compound of formula (Va), a compound of formula (Vb), a compound of formula (Vc), and a compound of formula (Vd). These compositions may, for example, be obtained by and/or obtainable by a combination of the bioconversion reaction described herein and the acid treatment step described herein.

For example, there is provided herein a composition comprising one, two or three of a compound of formula (Va), a compound of formula (Vb), and a compound of formula (Vc). These compositions may, for example, not comprise a compound of formula (Vd). These compositions may, for example, be obtained by and/or obtainable by a combination of the bioconversion reaction described herein and the acid treatment step described herein.

For example, there is provided herein a composition comprising a compound of formula (Va), a compound of formula (Vb), and a compound of formula (Vc), wherein:

- the compound of formula (Va) is present in the composition in an amount ranging from about 20.0 wt % to less than about 40.0 wt %;
- the compound of formula (Vb) is present in the composition in an amount ranging from greater than about 40.0 wt % to about 70.0 wt %; and
- the compound of formula (Vc) is present in the composition in an amount ranging from about 5.0 wt % to about 15.0 wt %.

The composition may, for example, further comprise a compound of formula (Vd). For example, the compound of formula (Vd) may be present in the composition in an amount ranging from about 0.5 wt % to about 5.0 wt %, for example from about 1.0 wt % to about 5.0 wt % or from about 1.0 wt % to about 4.0 wt % or from about 1.0 wt % to about 3.0 wt %. Alternatively, the composition may not comprise a compound of formula (Vd).

The compound of formula (Va) may, for example, be present in the composition in an amount equal to or greater than about 20.0 wt %. For example, the compound of formula (Va) may be present in the composition in an amount equal to or greater than about 22.0 wt % or equal to or greater than about 24.0 wt % or equal to or greater than about 25.0 wt %. In certain embodiments, the compound of formula (Va) may be present in the composition in an amount equal to or greater than about 25.0 wt %, equal to or greater than about 30.0 wt %, equal to or greater than about 35.0 wt %, equal to or greater than about 40.0 wt. % or equal to or greater than about 45.0 wt. %. The amounts of 25.0 wt. % or greater of compound (Va) may in particular be obtained when the initial bioconversion reaction uses the variant alcohol dehydrogenase of the eighth aspect of the present invention.

The compound of formula (Va) may, for example, be present in the composition in an amount less than about 50.0 wt. %, less than about 45.0 wt. % or less than about 40.0 wt %. For example, the compound of formula (Va) may be present in the composition in an amount equal to or less than about 38.0 wt % or equal to or less than about 36.0 wt % or equal to or less than about 35.0 wt % or equal to or less than about 34.0 wt % or equal to or less than about 32.0 wt % or equal to or less than about 30.0 wt % or equal to or less than about 28.0 wt %.

The compound of formula (Va) may, for example, be present in the composition in an amount ranging from about 20.0 wt % to less than about 40.0 wt % or from about 20.0 wt % to about 35.0 wt % or from about 22.0 wt % to about 30.0 wt % or from about 24.0 wt % to about 28.0 wt %. In certain embodiments, the compound of formula (Va) may, for example, be present in the composition in an amount ranging from about 25.0 wt % to less than about 50.0 wt % or from about 30.0 wt % to about 45.0 wt %.

The compound of formula (Vb) may, for example, be present in the composition in an amount greater than about 40.0 wt %. For example, the compound of formula (Vb) may be present in the composition in an amount equal to or greater than about 45.0 wt % or equal to or greater than about 50.0 wt % or equal to or greater than about 55.0 wt % or equal to or greater than about 60.0 wt %.

The compound of formula (Vb) may, for example, be present in the composition in an amount equal to or less than about 70.0 wt %. For example, the compound of formula (Vb) may be present in the composition in an amount equal to or less than about 68.0 wt % or equal to or less than about 66.0 wt % or equal to or less than about 65.0 wt %.

The compound of formula (Vb) may, for example, be present in the composition in an amount ranging from greater than about 40.0 wt % to about 70.0 wt % or from about 50.0 wt % to about 70.0 wt % or from about 60.0 wt % to about 70.0 wt %.

The compound of formula (Vc) may, for example, be present in the composition in an amount equal to or greater than about 5.0 wt %. For example, the compound of formula (Vc) may be present in the composition in an amount equal to or greater than about 6.0 wt % or equal to or greater than about 8.0 wt % or equal to or greater than about 10.0 wt %.

The compound of formula (Vc) may, for example, be present in the composition in an amount equal to or less than about 15.0 wt %. For example, the compound of formula (Vc) may be present in the composition in an amount equal to or less than about 14.0 wt % or equal to or less than about 13.0 wt % or equal to or less than about 12.0 wt %.

The compound of formula (Vc) may, for example, be present in the composition in an amount ranging from about 5.0 wt % to about 15.0 wt % or from about 8.0 wt % to about 15.0 wt % or from about 10.0 wt % to about 15.0 wt %.

The composition may, for example, comprise:

- from about 20.0 wt % to about 40.0 wt % of a compound of formula (Va); and
- from about 55.0 wt % to about 70.0 wt % of a compound of formula (Vb); and
- from about 5.0 wt % to about 15.0 wt % of a compound of formula (Vc).

The composition may, for example, comprise:

from about 20.0 wt % to about 40.0 wt % of a compound of formula (Va); and from about 60.0 wt % to about 70.0 wt % of a compound of formula (Vb); and from about 8.0 wt % to about 15.0 wt % of a compound of formula (Vc).

The composition may, for example, comprise:

from about 20.0 wt % to about 30.0 wt % of a compound of formula (Va); and from about 55.0 wt % to about 70.0 wt % of a compound of formula (Vb); and from about 5.0 wt % to about 15.0 wt % of a compound of formula (Vc).

The composition may, for example, comprise:

from about 20.0 wt % to about 30.0 wt % of a compound of formula (Va); and from about 60.0 wt % to about 70.0 wt % of a compound of formula (Vb); and from about 8.0 wt % to about 15.0 wt % of a compound of formula (Vc).

The composition may, for example, comprise:

from about 22.0 wt % to about 28.0 wt % of a compound of formula (Va); and from about 60.0 wt % to about 70.0 wt % of a compound of formula (Vb); and from about 8.0 wt % to about 15.0 wt % of a compound of formula (Vc).

The wt % ranges described herein may, for example, be based on the total weight of the total compounds of formula (V) in the composition.

The compound of formula (Va) may, for example, have an enantiomeric excess of the (R) enantiomer (configuration at C3 bearing the methyl group) equal to or greater than about 25.0%. For example, the compound of formula (Va) may have an enantiomeric excess of the (R) enantiomer equal to or greater than about 30.0% or equal to or greater than about 35.0% or equal to or greater than about 40.0% or equal to or greater than about 45.0% or equal to or greater than about 50.0% or equal to or greater than about 55.0% or equal to or greater than about 60.0%. In some embodiments, the compound of formula (Va) may have an enantiomeric excess of the (R) enantiomer equal to or greater than about 60.0% or equal to or greater than about 70.0% or equal to or greater than about 75.0% or equal to or greater than about 80.0% or equal to or greater than about 85.0% or equal to or greater than about 90.0% or equal to or greater than about 95.0%. The enantiomeric excess of (R) enantiomer for compound (Va) of 65.0% or greater may in particular be obtained when the initial bioconversion reaction uses the variant alcohol dehydrogenase of the eighth aspect of the present invention.

The compound of formula (Va) may, for example, have an enantiomeric excess of the (R) enantiomer (configuration at C3 bearing the methyl group) equal to or less than 100.0%. For example, the compound of formula (Va) may have an enantiomeric excess of the (R) enantiomer equal to or less than about 99.0% or equal to or less than about 98.0% or equal to or less than about 95.0% or equal to or less than about 90.0% or equal to or less than about 85.0% or equal to or less than about 80.0%.

The compound of formula (Va) may, for example, have an enantiomeric excess of the (R) enantiomer (configuration at C3 bearing the methyl group) ranging from about 25.0% to about 100.0% or from about 30.0% to about 100.0% or from about 50.0% to about 100.0% or from about 60.0% to about 95.0% or from about 60.0% to about 90.0%. In certain embodiments, the compound of formula (Va) may, for example, have an enantiomeric excess of the (R) enantiomer (configuration at C3 bearing the methyl group) ranging from about 60.0% to about 100.0% or from about 80.0% to about 100.0% or from about 90.0% to about 100.0% or from about 90.0% to about 99.0%. The enantiomeric excess of (R) enantiomer for compound (Va) in the range of about 60.0% to about 100.0% may in particular be obtained when the initial bioconversion reaction uses the variant alcohol dehydrogenase of the eighth aspect of the present invention.

The compound of formula (Vb) may, for example, have an enantiomeric excess of the (R) enantiomer (configuration at C3 bearing the methyl group) equal to or greater than about 25.0%. For example, the compound of formula (Vb) may have an enantiomeric excess of the (R) enantiomer equal to or greater than about 30.0% equal to or greater than about 35.0% or equal to or greater than about 40.0% or equal to or greater than about 45.0% or equal to or greater than about 50.0% or equal to or greater than about 55.0% or equal to or greater than about 60.0%.

The compound of formula (Vb) may, for example, have an enantiomeric excess of the (R) enantiomer (configuration at C3 bearing the methyl group) equal to or less than 100.0%. For example, the compound of formula (Vb) may have an enantiomeric excess of the (R) enantiomer equal to or less than about 99.0% or equal to or less than about 98.0% or equal to or less than about 95.0% or equal to or less than about 90.0% or equal to or less than about 85.0% or equal to or less than about 80.0%.

The compound of formula (Vb) may, for example, have an enantiomeric excess of the (R) enantiomer (configuration at C3 bearing the methyl group) ranging from about 25.0% to about 100.0% or from about 30.0% to about 100.0% or from about 50.0% to about 100.0% or from about 60.0% to about 95.0% or from about 60.0% to about 90.0%.

The compound of formula (Vc) may, for example, have an enantiomeric excess of the (S) enantiomer (configuration at C3 bearing the methyl group) equal to or greater than about 25.0%. For example, the compound of formula (Vc) may have an enantiomeric excess of the (S) enantiomer equal to or greater than about 30.0% equal to or greater than about 35.0% or equal to or greater than about 40.0% or equal to or greater than about 45.0% or equal to or greater than about 50.0% or equal to or greater than about 55.0% or equal to or greater than about 60.0%.

The compound of formula (Vc) may, for example, have an enantiomeric excess of the (S) enantiomer (configuration at C3 bearing the methyl group) equal to or less than 100.0%. For example, the compound of formula (Vc) may have an enantiomeric excess of the (S) enantiomer equal to or less than about 99.0% or equal to or less than about 98.0% or equal to or less than about 95.0% or equal to or less than about 90.0% or equal to or less than about 85.0% or equal to or less than about 80.0%.

The compound of formula (Vc) may, for example, have an enantiomeric excess of the (S) enantiomer (configuration at C3 bearing the methyl group) ranging from about 25.0% to about 100.0% or from about 30.0% to about 100.0% or from about 50.0% to about 100.0% or from about 60.0% to about 95.0% or from about 60.0% to about 90.0%.

The compound of formula (Vd) may, for example, have an enantiomeric excess of the (S) enantiomer (configuration at C3 bearing the methyl group) equal to or greater than about 25.0%. For example, the compound of formula (Vd) may have an enantiomeric excess of the (S) enantiomer equal to or greater than about 30.0% or equal to or greater than about 35.0% or equal to or greater than about 40.0% or equal to or greater than about 45.0% or equal to or greater than about 50.0% or equal to or greater than about 55.0% or equal to or greater than about 60.0%.

The compound of formula (Vd) may, for example, have an enantiomeric excess of the (S) enantiomer (configuration at C3 bearing the methyl group) equal to or less than 100.0%. For example, the compound of formula (Vd) may have an enantiomeric excess of the (S) enantiomer equal to or less than about 99.0% or equal to or less than about 98.0% or equal to or less than about 95.0% or equal to or less than about 90.0% or equal to or less than about 85.0% or equal to or less than about 80.0%.

The compound of formula (Vd) may, for example, have an enantiomeric excess of the (S) enantiomer (configuration at C3 bearing the methyl group) ranging from about 25.0% to about 100.0% or from about 30.0% to about 100.0% or from about 50.0% to about 100.0% or from about 60.0% to about 95.0% or from about 60.0% to about 90.0%.

Enantiomeric excess (e.e.) refers to the excess of one enantiomer over the other, expressed as a percentage of the whole and calculated by the formula below wherein R and S are respectively the fractions of the R and S enantiomers in a mixture, $$\text{e.e. of } (R) \text{ enantiomer} = ((R-S)/(R+S)) \times 100$$

$$\text{e.e. of } (S) \text{ enantiomer} = ((S-R)/(R+S)) \times 100$$

There is also provided herein a composition comprising:

- from 35 to 55% w/w of a compound of formula (Va) having an enantiomeric excess of the (R) enantiomer (configuration at C3 bearing the methyl group) of less than 80%;
- from 27 to 40% w/w of a compound of formula (Vb) having an enantiomeric excess of the (R) enantiomer (configuration at C3 bearing the methyl group) of less than 80%;
- from 3 to 20% w/w of a compound of formula (Vc) having an enantiomeric excess of the (S) enantiomer (configuration at C3 bearing the methyl group) of less than 80%; and
- from 0 to 5% w/w of a compound of formula (Vd) having an enantiomeric excess of the (S) enantiomer (configuration at C3 bearing the methyl group) of less than 80%.

The composition may, for example, comprise equal to or greater than about 35.0 wt % of a compound of formula (Va) having an enantiomeric excess of the (R) enantiomer of less than about 80.0%. For example, the composition may comprise equal to or greater than about 40.0 wt % of a compound of formula (Va) having an enantiomeric excess of the (R) enantiomer of less than about 80.0%. The composition may, for example, comprise equal to or less than about 55.0 wt % of a compound of formula (Va) having an enantiomeric excess of the (R) enantiomer of less than about 80.0%. For example, the composition may comprise equal to or less than about 50.0 wt % of a compound of formula (Va) having an enantiomeric excess of the (R) enantiomer of less than about 80.0%. For example, the composition may comprise from about 35.0 wt % to about 55.0 wt % or from about 40.0 wt % to about 50.0 wt % of a compound of formula (Va) having an enantiomeric excess of the (R) enantiomer of less than about 80.0%. The compound of formula (Va) may, for example, have an enantiomeric excess of the (R) enantiomer ranging from about 50.0% to less than about 80.0% or from about 60.0% to less than about 80.0%.

Alternatively, the composition may, for example, comprise equal to or greater than about 35.0 wt % of a compound of formula (Va) having an enantiomeric excess of the (R) enantiomer of equal to or greater than about 80.0%. For example, the composition may comprise equal to or greater than about 40.0 wt % of a compound of formula (Va) having an enantiomeric excess of the (R) enantiomer equal to or greater than about 80.0%. The composition may, for example, comprise equal to or less than about 55.0 wt % of a compound of formula (Va) having an enantiomeric excess of the (R) enantiomer of equal to or greater than about 80.0%. For example, the composition may comprise equal to or less than about 50.0 wt % of a compound of formula (Va) having an enantiomeric excess of the (R) enantiomer of equal to or greater than about 80.0%. For example, the composition may comprise from about 35.0 wt % to about 55.0 wt % or from about 40.0 wt % to about 50.0 wt % of a compound of formula (Va) having an enantiomeric excess of the (R) enantiomer of equal to or greater than about 80.0%. The compound of formula (Va) may, for example, have an enantiomeric excess of the (R) enantiomer ranging from about 80.0% to equal to or less than about 100.0% or from about 90.0% to equal to or less than about 100.0%.

The composition may, for example, comprise equal to or greater than about 27.0 wt % of a compound of formula (Vb) having an enantiomeric excess of the (R) enantiomer of less than about 80.0%. For example, the composition may comprise equal to or greater than about 30.0 wt % of a compound of formula (Vb) having an enantiomeric excess of the (R) enantiomer of less than about 80.0%. The composition may, for example, comprise equal to or less than about 40.0 wt % of a compound of formula (Vb) having an enantiomeric excess of the (R) enantiomer of less than about 80.0%. For example, the composition may comprise equal to or less than about 35.0 wt % of a compound of formula (Vb) having an enantiomeric excess of the (R) enantiomer of less than about 80.0%. For example, the composition may comprise from about 27.0 wt % to about 40.0 wt % or from about 30.0 wt % to about 35.0 wt % of a compound of formula (Vb) having an enantiomeric excess of the (R) enantiomer of less than about 80.0%. The compound of formula (Vb) may, for example, have an enantiomeric excess of the (R) enantiomer ranging from about 50.0% to less than about 80.0% or from about 60.0% to less than about 80.0%.

The composition may, for example, comprise equal to or greater than about 3.0 wt % of a compound of formula (Vc) having an enantiomeric excess of the (S) enantiomer of less than about 80.0%. For example, the composition may comprise equal to or greater than about 5.0 wt % or equal to or greater than about 10.0 wt % of a compound of formula (Vc) having an enantiomeric excess of the (S) enantiomer of less than about 80.0%. The composition may, for example, comprise equal to or less than about 20.0 wt % of a compound of formula (Vc) having an enantiomeric excess of the (S) enantiomer of less than about 80.0%. For example, the composition may comprise equal to or less than about 15.0 wt % of a compound of formula (Vc) having an enantiomeric excess of the (S) enantiomer of less than about 80.0%. For example, the composition may comprise from about 3.0 wt % to about 20.0 wt % or from about 5.0 wt % to about 15.0 wt % of a compound of formula (Vc) having an enantiomeric excess of the (S) enantiomer of less than about 80.0%. The compound of formula (Vc) may, for example, have an enantiomeric excess of the (S) enantiomer ranging from about 50.0% to less than about 80.0% or from about 60.0% to less than about 80.0%.

The composition may, for example, comprise equal to or greater than 0.0 wt % of a compound of formula (Vd) having an enantiomeric excess of the (S) enantiomer of less than about 80.0%. For example, the composition may comprise equal to or greater than about 0.5 wt % or equal to or greater than about 1.0 wt % of a compound of formula (Vd) having an enantiomeric excess of the (S) enantiomer of less than about 80.0%. The composition may, for example, comprise equal to or less than about 5.0 wt % of a compound of formula (Vd) having an enantiomeric excess of the (S) enantiomer of less than about 80.0%. For example, the composition may comprise equal to or less than about 4.0 wt % of a compound of formula (Vd) having an enantiomeric excess of the (S) enantiomer of less than about 80.0%. For example, the composition may comprise from 0.0 wt % to about 5.0 wt % or from about 0.5 wt % to about 5.0 wt % of a compound of formula (Vd) having an enantiomeric excess of the (S) enantiomer of less than about 80.0%. The compound of formula (Vd) may, for example, have an enantiomeric excess of the (S) enantiomer ranging from about 50.0% to less than about 80.0% or from about 60.0% to less than about 80.0%.

The reactions described herein may, for example, not proceed to completion. Therefore, the compositions described herein may further comprise unreacted starting materials. For example, the compositions obtained by and/or obtainable by the bioconversion reaction described herein may further comprise a compound of formula (I). For example, the compositions obtained by and/or obtainable by the bioconversion reaction followed by acidic treatment step may further comprise one or more of a compound of formula (I), a compound of formula (II), a compound of formula (III), and a compound of formula (IV).

Uses of the Compositions

There is further provided herein the use of the compositions described herein as a fragrance ingredient. In addition, there is further provided herein a consumer product comprising a composition as described herein. In particular, the composition may be a composition comprising one or more compounds of formula (V), obtained via a bioconversion reaction followed by a dehydration step.

Thus, there is also provided herein a fragrance composition comprising a composition as described herein. By “fragrance composition” is meant any composition comprising a composition as described herein and a base material.

As used herein, the “base material” includes all known fragrance ingredients selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, diluents, and other auxiliary agents commonly used in the art.

Fragrance ingredients known to the art are readily available commercially from the major fragrance manufacturers. Non-limiting examples of such ingredients include:

- essential oils and extracts, e.g. castoreum, costus root oil, oak moss absolute, geranium oil, tree moss absolute, basil oil, fruit oils, such as bergamot oil and mandarine oil, myrtle oil, palmarose oil, patchouli oil, petitgrain oil, jasmine oil, rose oil, sandalwood oil, wormwood oil, lavender oil and/or ylang-ylang oil;
- alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
- aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl) ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl) ethanone); Isoraldeine® ((E)-3-methyl-4-(2,6,6-trimethylcyclohex-2-en-1-yl)but-3-en-2-one); 3-(4-isobutyl-2-methylphenyl)propanal; maltol; methyl cedryl ketone; methylionone; verbenone; and/or vanillin;
- ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo[4.1.0]heptane-2,5'-[1,3]dioxane]);
- macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and
- heterocycles, e.g. isobutylquinoline (2-isobutylquinoline).

As used herein, “carrier material” means a material which is practically neutral from an odorant point of view, i.e. a material that does not significantly alter the organoleptic properties of odorants.

By “diluents” is meant any diluent conventionally used in conjunction with odorants, such as diethyl phthalate (DEP), dipropylene glycol (DPG), isopropyl myristate (IPM), triethyl citrate (TEC) and alcohol (e.g. ethanol).

The term “auxiliary agent” refers to ingredients that might be employed in a fragrance composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same, such as anti-oxidant adjuvant. Said anti-oxidant may be selected, for example, from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

It might also be an ingredient that provides additional benefits such as imparting colour or texture. It might also be an ingredient that imparts light resistance or chemical stability to one or more ingredients contained in a fragrance composition.

A detailed description of the nature and type of auxiliary agent commonly used in fragrance compositions containing same cannot be exhaustive, but it has to be mentioned that said ingredients are well known to a person skilled in the art.

Various applications for the compositions described herein include but are not limited to a fine fragrance or a consumer product such as fabric care, toiletries, beauty care and cleaning products, detergent products, and soap products.

There is also provided herein a consumer product comprising a composition as described herein, including any embodiment thereof. The consumer product may, for example, be a cosmetic product (e.g. an eau de parfum or eau de toilette), a cleaning product, a detergent product, or a soap product.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. The term "comprising" also means "including" as well as "consisting" e.g. a composition "comprising" X may consist exclusively of X or may include something additional e.g. X+Y. It must be noted also that, as used in this specification and the appended claims, the singular forms "a", "an" and "the" include plural referents unless the content clearly dictates otherwise. By way of example, a reference to "a gene" or "an enzyme" is a reference to "one or more genes" or "one or more enzymes".

It is to be understood that this disclosure is not limited to the particular methodology, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by the person skilled in the art. In accordance with the present disclosure there may be conventional molecular biology, microbiology, and recombinant DNA techniques employed which are within the skill of the art.

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting. Preferably, the terms used herein are defined as described in "A multilingual glossary of biotechnological terms: (IUPAC Recommendations)", Leuenberger, H. G. W, Nagel, B. and Kolbl, H. eds. (1995), Helvetica Chimica Acta, CH-4010 Basel, Switzerland).

Several documents are cited throughout the text of this specification. Each of the documents cited herein (including all patents, patent applications, scientific publications, manufacturer's specifications, instructions, GenBank Accession Number sequence submissions etc.), whether supra or infra, is hereby incorporated by reference in its entirety.

The examples described herein are illustrative of the present disclosure and are not intended to be limitations thereon. Different embodiments of the present disclosure have been described according to the present disclosure. Many modifications and variations may be made to the techniques described and illustrated herein without departing from the spirit and scope of the disclosure. Accordingly, it should be understood that the examples are illustrative only and are not limiting upon the scope of the disclosure.

EXAMPLES

Example 1: Biotransformation with KRED-P1-B10 (from Codexis Inc., USA) (Isopropanol Regeneration) and Acidic Treatment with pTSA Biotransformation A flask was charged with Codexis KRED-P1-B10 (500 mg) dissolved in 100 mM potassium phosphate buffer, pH 7.5 (44 mL). Solutions of NADP disodium salt (39.4 mg) in 100 mM potassium phosphate buffer pH 7.5 (1 mL) and 3-methylcyclopentadecane-1,5-dione (630 mg) in iPrOH (5 mL) were added. The reaction mixture was stirred at 30° C. for 26 h. The reaction mixture was extracted with 100 ml MTBE. To facilitate phase separation, the mixture was centrifuged. The combined organic layers were washed with 25 ml water and 25 mL brine, dried over magnesium sulfate, and the solvent was evaporated. The crude product (0.52 g, viscous yellow oil) was analyzed via GC, revealing 64% enol ether (compound of formula (IV)), 14% diketone (compound of formula (I)), 1% hydroxy ketone (compound of formula (II)), and 2% diol (compound of formula (VII)) (relative GC area %).

$^{13}C$-NMR (400 MHZ, $CDCl_3$, regular+DEPT90+DEPT135): δ (ppm)=22.93, 23.24, 23.43, 23.62, 24.14, 24.23, 24.36, 24.53, 25.50, 25.76, 26.00, 26.10, 26.18, 26.42, 26.55, 26.59, 26.66, 26.78, 26.82, 26.96, 27.34, 27.62, 27.76, 29.70, 33.50, 34.65, 35.55, 39.89, 40.18, 41.62, 41.89, 42.18, 42.56, 43.95, 48.87, 50.11, 50.99, 67.51, 68.59, 70.51, 76.71, 77.02, 77.34, 97.59 (hemi acetal quaternary carbon), 211.14 (diketone carbonyls), 211.88 (hydroxyl ketone carbonyl).

The NMR data revealed that no double bond was present in the crude product, but instead a quaternary carbon was detected, meaning that the enol ether (which has a double bond) formed through thermal dehydration of the hemi acetal (which has a quaternary carbon).

Acidic Treatment

A flask was charged with a solution of the crude product from the biotransformation (0.48 g) in dichloromethane (10 mL). pTSA (72.6 mg) was added and the reaction mixture was heated to reflux. After 18 h and 42 h, additional pTSA (37.4 mg and 73.3 mg) was added. After a total of 64 h, only 6% of starting material was detected and the reaction mixture was poured into 25 mL sat. $NaHCO_3$ solution and extracted twice with 25 mL MTBE each. Both organic phases were washed with 25 mL $H_2O$, combined, dried over $MgSO_4$, filtrated and the solvent was evaporated. The resulting crude product (0.45 g) was purified by flash chromatography ($SiO_2$, heptane/MTBE). The main fraction was analyzed on chiral GC, giving mainly (S)-5-E-muscenone (Table 1).

The identity of the products was analyzed by gas chromatography.

TABLE 1

| Peak (chiral GC) | Isomer | Ratio (%) | Combined (%) | ee (%) |
|---|---|---|---|---|
| 1 (105.7 min) | (S,E)-3-methyl-cyclopentadec-4-enone | 1.2 | 9.2 | 73.9 (R) |
| 2 (106.7 min) | (R,E)-3-methyl-cyclopentadec-4-enone | 8.0 | | |
| 3 (111.7 min) | (S,E)-3-methyl-cyclopentadec-5-enone | 45.5 | 53.6 | 69.8 (S) |
| 4 (112.7 min) | (R,E)-3-methyl-cyclopentadec-5-enone | 8.1 | | |
| 5 (115.3 min) | (S,Z)-3-methyl-cyclopentadec-5-enone | 32.2 | 37.2 | 73.1 (S) |
| 6 (116.2 min) | (R,Z)-3-methyl-cyclopentadec-5-enone | 5.0 | | |

Example 2: Biotransformation With PRO-KRED(124) (From Prozomix Limited, UK) (GDH Regeneration) and Acidic Treatment With pTSA Biotransformation A flask was charged with Prozomix PRO-KRED(124) (500 mg) in 100 mM potassium phosphate buffer pH 7 (41.5 mL). Solutions of beta-NAD (33.2 mg) in 100 mM potassium phosphate buffer pH 7 (1 mL), NADP disodium salt (39.4 mg) in 100 mM potassium phosphate buffer pH 7 (1 mL), and Codexis -CDX-901 (50 mg) in 100 mM potassium phosphate buffer pH 7 (1 mL) were successively added followed by a solution of 1.6 M D-glucose in water (3.1 mL). Finally, a solution of 3-methylcyclopentadecane-1,5-dione (505 mg) in dimethyl sulfoxide (2.5 mL) was added. The reaction mixture was stirred at 30° C. for 69 h and the pH was continuously adjusted to pH 7.0 by titration with 2 M NaOH. The reaction mixture was extracted with 100 mL MTBE. To facilitate phase separation, the mixture was centrifuged. The combined organic layers were washed with 25 ml water and 25 mL brine, dried over magnesium sulfate, and the solvent was evaporated. The crude product (0.43 g) was analyzed via GC (without internal standard), revealing 13% enol ether (compound of formula (IV)), 5% diketone (compound of formula (I)), and 82% hydroxy ketone (compound of formula (II)) (relative GC area %). No diol was detected.

Acidic Treatment

A flask was charged with a solution of the crude product from the biotransformation (0.43 g) in toluene (15 mL). pTSA (165 mg) was added and the reaction mixture was heated to 80° C. After 1 h, the reaction was analyzed via GC and contained 23% enol ether (compound of formula (IV)), 7% (E)-4-muscenone (compound of formula (Vc)), 46% (E)-5-muscenone (compound of formula (Vb)), 18% (Z)-5-muscenone (compound of formula (Va)) and 2% hydroxy ketone (compound of formula (II)) indicating that hydroxy ketone (compound of formula (II)) is first converted into the enol ether (compound of formula (IV)) before ring opening to the muscenone isomers). After another 1 h, the reaction was complete, showing 11% (E)-4-muscenone (compound of formula (Vc)), 63% (E)-5-muscenone (compound of formula (Vb)), 25% (Z)-5-muscenone (compound of formula (Va)) (Table 2). The reaction mixture was poured into 25 mL sat. $NaHCO_3$ solution and extracted twice with 25 mL MTBE each. Both organic phases were washed with 25 mL $H_2O$, combined, dried over $MgSO_4$, filtrated and the solvent was evaporated. The resulting crude product (0.41 g) was purified by flash chromatography ($SiO_2$, heptane/MTBE) with the second fraction being enriched in (R)-5-Z-muscenone (103 mg, Table 3).

The identity of the products was analyzed by gas chromatography.

TABLE 2

| Peak (chiral GC) | Isomer | Ratio (%) | Combined (%) | ee (%) |
|---|---|---|---|---|
| 1 (105.5 min) | (S,E)-3-methyl-cyclopentadec-4-enone | 7.9 | 11.5 | 37.4 (S) |
| 2 (106.5 min) | (R,E)-3-methyl-cyclopentadec-4-enone | 3.6 | | |
| 3 (111.5 min) | (S,E)-3-methyl-cyclopentadec-5-enone | 20.1 | 63.3 | 36.5 (R) |
| 4 (112.5 min) | (R,E)-3-methyl-cyclopentadec-5-enone | 43.2 | | |
| 5 (115.1 min) | (S,Z)-3-methyl-cyclopentadec-5-enone | 8.0 | 25.2 | 36.5 (R) |
| 6 (116.0 min) | (R,Z)-3-methyl-cyclopentadec-5-enone | 17.2 | | |

TABLE 3

| Peak (chiral GC) | Isomer | Ratio (%) | Combined (%) | ee (%) |
|---|---|---|---|---|
| 1 (105.5 min) | (S,E)-3-methyl-cyclopentadec-4-enone | 13.5 | 19.7 | 37.1 (S) |
| 2 (106.5 min) | (R,E)-3-methyl-cyclopentadec-4-enone | 6.2 | | |
| 3 (111.5 min) | (S,E)-3-methyl-cyclopentadec-5-enone | 9.6 | 30.0 | 36.0 (R) |
| 4 (112.5 min) | (R,E)-3-methyl-cyclopentadec-5-enone | 20.4 | | |
| 5 (115.1 min) | (S,Z)-3-methyl-cyclopentadec-5-enone | 15.9 | 50.3 | 36.8 (R) |
| 6 (116.0 min) | (R,Z)-3-methyl-cyclopentadec-5-enone | 34.4 | | |

Example 3: Biotransformation with EMIN025 (from Enzymaster (Ningbo) Bio-Engineering Co., Ltd., China) (GDH Regeneration) and Acidic Treatment by pTSA Biotransformation A flask was charged with Enzymaster EMIN025 (250 mg) in 100 mM potassium phosphate buffer pH 7 (41.5 mL). Solutions of beta-NAD (33.2 mg) in 100 mM potassium phosphate buffer pH 7 (1 mL), NADP disodium salt (39.4 mg) in 100 mM potassium phosphate buffer pH 7 (1 mL), and Codexis GDH CDX-901 (50 mg) in 100 mM potassium phosphate buffer pH 7 (1 mL) were successively added followed by a solution of 1.6 M D-glucose in water (3.1 mL). Finally, a solution of 3-methylcyclopentadecane-1,5-dione (505 mg) in dimethyl sulfoxide (2.5 mL) was added. The reaction mixture was stirred at 30° C. while continuously adjusting the pH to pH 7.0 by titration with 2 M NaOH. After 53 h further portions of NADP disodium salt (19.6 mg), beta-NAD (16.6 mg), GDH CDX-901 (25 mg) and Enzymaster EMIN025 (125 mg) were successively added, and the reaction mixture was further allowed to stir at 30° C. After an additional 23 h, the reaction mixture was extracted with 100 mL MTBE. To facilitate phase separation, the mixture was centrifuged. The combined organic layers were washed with 25 ml water and 25 mL brine, dried over magnesium sulfate, and the solvent was evaporated. The crude product (0.35 g) was analyzed via GC, revealing 75% enol ether (compound of formula (IV)), 12% diketone (compound of formula (I)), and 13% diol (compound of formula (VII)) (relative GC area %).

Acidic Treatment

A flask was charged with a solution of the crude product from the biotransformation (0.35 g) in toluene (15 mL). pTSA (134 mg) was added and the reaction mixture was heated to 80° C. for 1.5 h. The reaction mixture was poured into 25 mL sat. $NaHCO_3$ solution and extracted twice with 25 mL MTBE each. Both organic phases were washed with 25 mL $H_2O$, combined, dried over $MgSO_4$, filtrated and the solvent was evaporated. The resulting crude product (0.34 g) was purified by flash chromatography ($SiO_2$, heptane/MTBE). The main fraction was analyzed on chiral GC, giving mainly (R)-5-E-muscenone (Table 4).

The identity of the products was analyzed by gas chromatography.

TABLE 4

| Peak (chiral GC) | Isomer | Ratio (%) | Combined (%) | ee (%) |
|---|---|---|---|---|
| 1 (105.7 min) | (S,E)-3-methyl-cyclopentadec-4-enone | 7.5 | 11.6 | 29.3 (S) |
| 2 (106.7 min) | (R,E)-3-methyl-cyclopentadec-4-enone | 4.1 | | |
| 3 (111.7 min) | (S,E)-3-methyl-cyclopentadec-5-enone | 21.4 | 62.4 | 31.4 (R) |
| 4 (112.7 min) | (R,E)-3-methyl-cyclopentadec-5-enone | 41.0 | | |
| 5 (115.3 min) | (S,Z)-3-methyl-cyclopentadec-5-enone | 9.0 | 26.0 | 30.8 (R) |
| 6 (116.2 min) | (R,Z)-3-methyl-cyclopentadec-5-enone | 17.0 | | |

Example 4: Biotransformation with EMIN027 (from Enzymaster (Ningbo) Bio-Engineering Co., Ltd., China) Having the Amino Acid Sequence of SEQ ID NO: 1 (Isopropanol Regeneration) and Acidic Treatment by pTSA Biotransformation A flask was charged with an alcohol dehydrogenase having the amino acid sequence of SEQ ID NO: 1 (500 mg) dissolved in 100 mM potassium phosphate buffer, pH 7.5 (43 mL). Solutions of beta-NAD (33.4 mg) in 100 mM potassium phosphate buffer pH 7.5 (1 mL), NADP disodium salt (39.4 mg) in 100 mM potassium phosphate buffer pH 7.5 (1 mL) and 3-methylcyclopentadecane-1,5-dione (505 mg) in iPrOH (5 mL) were added. The reaction mixture was stirred at 30° C. for 88 h. The reaction mixture was extracted with 100 mL MTBE. To facilitate phase separation, the mixture was centrifuged. The combined organic layers were washed with 25 mL water and 25 ml brine, dried over magnesium sulfate, and the solvent was evaporated. The crude product (0.36 g) was analyzed via GC, revealing 78% enol ether (compound of formula (IV)) and 18% remaining diketone (compound of formula (I)) (relative GC area %).

```
SEQ ID NO: 1:
MDGFLSGFDGRAAVVTGGASGIGLATATEFARRGARLVLSDVDQP

ALEQAVNGLRGQGFDAHGVVCDVRHLDEMVRLADEAFRLLGGVDV

VFSNAGIVVAGPLAQMNHDDWRWVIDIDLWGSIHAVEAFLPRLLE

QGTGGHIAFTASFAGLVPNAGLGTYGVAKYGVVGLAETLAREVKP
```

-continued

```
NGIGVSVLCPMVVETKLVSNSERIRGADYGMSATPEGAFGPLPTQ

DESVSADDVARLTADAILANRLYILPHAAARESIRRRFERIDRTF

DEQAAEGWTH
(NCBI accession number: WP_003873027.1)
```

Acidic Treatment

A flask was charged with a solution of the crude product from the biotransformation (0.35 g) in toluene (15 mL). pTSA (136 mg) was added and the reaction mixture was heated to 80° C. for 1.5 h. The reaction mixture was poured into 25 mL sat. $NaHCO_3$ solution and extracted twice with 25 mL MTBE each. Both organic phases were washed with 25 mL $H_2O$, combined, dried over $MgSO_4$, filtrated and the solvent was evaporated. The resulting crude product (0.35 g) was purified by flash chromatography ($SiO_2$, heptane/MTBE). The main fraction (180 mg) was analyzed on chiral GC, giving mainly (R)-5-E-muscenone (Table 5).

The identity of the products was analyzed by gas chromatography.

TABLE 5

| Peak (chiral GC) | Isomer | Ratio (%) | Combined (%) | ee (%) |
|---|---|---|---|---|
| 1 (105.7 min) | (S,E)-3-methylcyclopentadec-4-enone | 9.3 | 11.0 | 63.6 (S) |
| 2 (106.7 min) | (R,E)-3-methylcyclopentadec-4-enone | 2.3 | | |
| 3 (111.7 min) | (S,E)-3-methylcyclopentadec-5-enone | 11.8 | 61.8 | 62.0 (R) |
| 4 (112.7 min) | (R,E)-3-methylcyclopentadec-5-enone | 50.1 | | |
| 5 (115.3 min) | (S,Z)-3-methylcyclopentadec-5-enone | 4.8 | 27.2 | 62.1 (R) |
| 6 (116.2 min) | (R,Z)-3-methylcyclopentadec-5-enone | 21.7 | | |

Example 5: Screening of Dehydration/Rearrangement Conditions

The enol ether (compound of formula (IV), 250 mg) was dissolved in an organic solvent and subjected to different acids according to Table 6. The distribution of muscenone isomers (compound of formula (V)) was analyzed.

TABLE 6

| Acid | Conditions | E-4 isomer (Formula (Vc)) [%] | E-5 isomer (Formula (Vb)) [%] | Z-5 isomer (Formula (Va)) [%] | Other isomers |
|---|---|---|---|---|---|
| $H_2SO_4$ | Toluene, 48 h, 40° C. | 8 | 37 | 18 | 0 |
| Montmorillonite K10 | Xylene, 16 h, 100° C. | 12 | 41 | 21 | 0 |
| Amberlyst 15 | Xylene, 32 h, 75° C. | 8 | 45 | 21 | 0 |
| Phenyl phosphoric acid | Xylene, 1 h, 100° C. | 8 | 52 | 27 | 0 |
| Poly phosphoric acid (1 eq) | Xylene, 20 h, 100° C. | 12 | 42 | 26 | 8 |
| Poly phosphoric acid (6 eq) | Xylene, 2.5 h, 100° C. | 8 | 31 | 23 | 16 |
| Phosphoric acid | Toluene, 3.5 h, 100° C. | 11 | 40 | 30 | 2 |
| para-toluene sulphonic acid (pTSA) | Toluene, 2 h, 80° C. | 8 | 48 | 21 | 0 |

Example 6: Biotransformation, Dehydration and Acidic Rearrangement of Diketone (Compound of Formula (I)) to Muscenone With Optimized MaADH Variants

Method

General Procedure 1: Biotransformation

The reactor was charged with freeze-dried cell-free extract of ADH (see TABLES 7 and 8) and dissolved in KPi buffer (Difference of other components to 25 mL total volume; 100 mM, pH 7.0). A stock solution of β-NAD (33.3 mg) in KPi buffer (1.5 mL, 100 mM, pH 7.0) was added followed by a solution consisting of 3-methylcyclopentadecane-1,5-ione (Compound of Formula (I), see TABLE 7) and iPrOH (see TABLE 7). The reaction mixture was stirred at 30° C. The reaction mixture was extracted with 25 ml MTBE, and the biphasic mixture was filtrated over a suction filter equipped with 5 g celite using another 25 mL MTBE. The resulting biphasic filtrate was separated and the aqueous phase was re-extracted with 25 mL MTBE. Both organic phases were washed with 25 mL water and 10 mL brine, combined, dried over $MgSO_4$, filtrated, and evaporated and analyzed via GC (TABLE 9).

TABLE 7

| Conditions | Substrate conc. [mM] | iPrOH [vol %] | Enzyme [g $L^{-1}$] |
|---|---|---|---|
| I | 40 | 10 | 10 |
| II | 40 | 10 | 5 |
| III | 40 | 20 | 2 |
| IV | 400 | 25 | 10 |
| V | 400 | 30 | 10 |

General Procedure 2: Acidic Rearrangement/Ring Opening With pTSA

A flask was charged with a solution of the crude product from the biotransformation in 10 mL dichloromethane. pTSA (72.6 mg) was added and the reaction mixture was heated to reflux. After 18 hours and 42 hours, additional pTSA (37.4 mg and 73.3 mg) was added. After a total of 64 hours, no intermediates were detected and the reaction mixture was poured into 25 mL sat. $NaHCO_3$ solution and extracted twice with 25 ml MTBE each. Both organic phases were washed with 25 mL $H_2O$, combined, dried over $MgSO_4$, filtrated and evaporated. The resulting crude product was purified by flash chromatography ($SiO_2$, heptane/MTBE) and analyzed via GC (TABLE 9).

General Procedure 3: Acidic Rearrangement/Ring Opening With Phosphoric Acid

A flask was charged with a solution of the crude product from the biotransformation in 25 mL toluene. Phosphoric acid (0.135 ml, 1.972 mmol) was added and the biphasic mixture was heated up to 100° C. for 3 hours. The reaction mixture was allowed to cool to room temperature and poured into 25 mL sat. $NaHCO_3$ solution under stirring. The aqueous phase was separated and re-extracted with 25 mL MTBE. Both organic phases were washed with 25 mL $H_2O$ and 10 mL brine, combined, dried over $MgSO_4$, filtrated and evaporated. The resulting crude product was purified by flash chromatography ($SiO_2$, heptane/MTBE) and analysed via GC (TABLE 9).

ADH Amino Acid Sequences

The ADH used was wild-type ADH from Mycobacterium avium (Uniprot ID: Q742X5, NCBI Acc. No.: WP_003873027.1, PDB ID: 3TJR) having the amino acid sequence as set out in SEQ ID NO: 1 or a variant having the amino acid sequence as set out in SEQ ID NO: 2 to SEQ ID NO: 16. Table 8 provides a summary of the substitutions in the variants with respect to the wild type amino acid sequence and FIG. 1 shows a comparison of the amino acid sequences of SEQ ID NO: 1 to 16, highlighting mutation points of interest.

TABLE 8

| Sequence ID | Mutation |
|---|---|
| 1 | None (wild-type) |
| 2 | N154V |
| 3 | V198L |
| 4 | T145N |
| 5 | T145N, N154V, V192Y, V198L |
| 6 | T145N, N154V, V198L |
| 7 | A100G, T145N, N154V, V192Y, V198L |
| 8 | V99H, A100G, M106T, T145N, N154V, G161T, V192Y, V198L |
| 9 | A100G, T145N, N154V, V192Y, K196N, V198L, S258R |
| 10 | A100G, T145N, N154V, V192Y, K196N, V198L, E227Y, S258R |
| 11 | R11V, F30M, V99H, A100G, M106T, L133M, T145N, N154V, G161T, V192Y, K196N, V198L, E227Y, S258R |
| 12 | R11V, F30L, V99H, A100G, M106T, T145N, N154V, G161T, V192Y, K196N, V198L, A213G, E227Y, S258R |
| 13 | R11V, F30M, A100G, T145N, N154V, V192Y, K196N, V198L, A213G, E227Y, S258R |

TABLE 8-continued

| Sequence ID | Mutation |
|---|---|
| 14 | R11V, F30M, A100G, L103I, Q105T, T145N, N154V, V192Y, E194Q, K196N, V198L, Y209G, M211P, A213G, E227Y, S258R |
| 15 | R11V, F30M, A100G, L103M, T145N, N154V, V192Y, E194K, K196N, V198L, Y209G, M211R, A213G, E227Y, S258R |
| 16 | R11V, F30M, A100G, L103M, Q105T, T145N, N154V, V192Y, E194K, K196N, V198L, Y209G, M211R, A213G, E227Y, S258R |

SEQ ID NO: 1 ("wild-type"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVAGPLAQMNHDDWRWVIDIDLWGSIHAVEAFLPRLLE
QGTGGHIAFTASFAGLVPNAGLGTYGVAKYGVVGLAETLAREVKP
NGIGVSVLCPMVVETKLVSNSERIRGADYGMSATPEGAFGPLPTQ
DESVSADDVARLTADAILANRLYILPHAAARESIRRRFERIDRTF
DEQAAEGWTH SEQ ID NO: 2 ("MaADH_var1"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVAGPLAQMNHDDWRWVIDIDLWGSIHAVEAFLPRLLE
QGTGGHIAFTASFAGLVPVAGLGTYGVAKYGVVGLAETLAREVKP
NGIGVSVLCPMVVETKLVSNSERIRGADYGMSATPEGAFGPLPTQ
DESVSADDVARLTADAILANRLYILPHAAARESIRRRFERIDRTF
DEQAAEGWTH SEQ ID NO: 3 ("MaADH_var2"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVAGPLAQMNHDDWRWVIDIDLWGSIHAVEAFLPRLLE
QGTGGHIAFTASFAGLVPNAGLGTYGVAKYGVVGLAETLAREVKP
NGIGVSVLCPMVVETKLLSNSERIRGADYGMSATPEGAFGPLPTQ
DESVSADDVARLTADAILANRLYILPHAAARESIRRRFERIDRTF
DEQAAEGWTH SEQ ID NO: 4 ("MaADH_var3"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVAGPLAQMNHDDWRWVIDIDLWGSIHAVEAFLPRLLE
QGTGGHIAFNASFAGLVPNAGLGTYGVAKYGWVGLAETLAREVKP
NGIGVSVLCPMVVETKLVSNSERIRGADYGMSATPEGAFGPLPTQ
DESVSADDVARLTADAILANRLYILPHAAARESIRRRFERIDRTF
DEQAAEGWTH -continued SEQ ID NO: 5 ("MaADH_var4"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVAGPLAQMNHDDWRWVIDIDLWGSIHAVEAFLPRLLE
QGTGGHIAFNASFAGLVPVAGLGTYGVAKYGVVGLAETLAREVKP
NGIGVSVLCPMYVETKLLSNSERIRGADYGMSATPEGAFGPLPTQ
DESVSADDVARLTADAILANRLYILPHAAARESIRRRFERIDRTF
DEQAAEGWTH SEQ ID NO: 6 ("MaADH_var5"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVAGPLAQMNHDDWRWVIDIDLWGSIHAVEAFLPRLLE
QGTGGHIAFNASFAGLVPVAGLGTYGVAKYGVVGLAETLAREVKP
NGIGVSVLCPMVVETKLLSNSERIRGADYGMSATPEGAFGPLPTQ
DESVSADDVARLTADAILANRLYILPHAAARESIRRRFERIDRTF
DEQAAEGWTH SEQ ID NO: 7 ("MaADH_var6"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVGGPLAQMNHDDWRWVIDIDLWGSIHAVEAFLPRLLE
QGTGGHIAFNASFAGLVPVAGLGTYGVAKYGVVGLAETLAREVKP
NGIGVSVLCPMYVETKLLSNSERIRGADYGMSATPEGAFGPLPTQ
DESVSADDVARLTADAILANRLYILPHAAARESIRRRFERIDRTF
DEQAAEGWTH SEQ ID NO: 8 ("MaADH_var7"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVHGGPLAQTNHDDWRWVIDIDLWGSIHAVEAFLPRLLE
QGTGGHIAFNASFAGLVPVAGLGTYTVAKYGVVGLAETLAREVKP
NGIGVSVLCPMYVETKLLSNSERIRGADYGMSATPEGAFGPLPTQ
DESVSADDVARLTADAILANRLYILPHAAARESIRRRFERIDRTF
DEQAAEGWTH SEQ ID NO: 9 ("MaADH_var8"):
MDGFLSGFDGRAAVVTGGASGIGLATATEFARRGARLVLSDVDQP
ALEQAVNGLRGQGFDAHGVVCDVRHLDEMVRLADEAFRLLGGVDV
VFSNAGIVVGGPLAQMNHDDWRWVIDIDLWGSIHAVEAFLPRLLE
QGTGGHIAFNASFAGLVPVAGLGTYGVAKYGVVGLAETLAREVKP
NGIGVSVLCPMYVETNLLSNSERIRGADYGMSATPEGAFGPLPTQ
DESVSADDVARLTADAILANRLYILPHAAARERIRRRFERIDRTF
DEQAAEGWTH SEQ ID NO: 10 ("MaADH_var9"):
MDGFLSGFDGRAAVVTGGASGIGLATATEFARRGARLVLSDVDQP
ALEQAVNGLRGQGFDAHGVVCDVRHLDEMVRLADEAFRLLGGVDV -continued

VFSNAGIVVGGPLAQMNHDDWRWVIDIDLWGSIHAVEAFLPRLLE

QGTGGHIAFNASFAGLVPVAGLGTYGVAKYGVVGLAETLAREVKP

NGIGVSVLCPMYVETNLLSNSERIRGADYGMSATPEGAFGPLPTQ

DYSVSADDVARLTADAILANRLYILPHAAARERIRRRFERIDRTF

DEQAAEGWTH

SEQ ID NO: 11 ("MaADH_var10"):
MDGFLSGFDGVAAVVTGGASGIGLATATEMARRGARLVLSDVDQP

ALEQAVNGLRGQGFDAHGVVCDVRHLDEMVRLADEAFRLLGGVDV

VFSNAGIVHGGPLAQTNHDDWRWVIDIDLWGSIHAVEAFLPRMLE

QGTGGHIAFNASFAGLVPVAGLGTYTVAKYGVVGLAETLAREVKP

NGIGVSVLCPMYVETNLLSNSERIRGADYGMSATPEGAFGPLPTQ

DYSVSADDVARLTADAILANRLYILPHAAARERIRRRFERIDRTF

DEQAAEGWTH

SEQ ID NO: 12 ("MaADH_var11"):
MDGFLSGFDGVAAVVTGGASGIGLATATELARRGARLVLSDVDQP

ALEQAVNGLRGQGFDAHGVVCDVRHLDEMVRLADEAFRLLGGVDV

VFSNAGIVHGGPLAQTNHDDWRWVIDIDLWGSIHAVEAFLPRLLE

QGTGGHIAFNASFAGLVPVAGLGTYTVAKYGVVGLAETLAREVKP

NGIGVSVLCPMYVETNLLSNSERIRGADYGMSGTPEGAFGPLPTQ

DYSVSADDVARLTADAILANRLYILPHAAARERIRRRFERIDRTF

DEQAAEGWTH

SEQ ID NO: 13 ("MaADH_var12"):
MDGFLSGFDGVAAVVTGGASGIGLATATEMARRGARLVLSDVDQP

ALEQAVNGLRGQGFDAHGVVCDVRHLDEMVRLADEAFRLLGGVDV

VFSNAGIVVGGPLAQMNHDDWRWVIDIDLWGSIHAVEAFLPRLLE

QGTGGHIAFNASFAGLVPVAGLGTYGVAKYGVVGLAETLAREVKP

NGIGVSVLCPMYVETNLLSNSERIRGADYGMSGTPEGAFGPLPTQ

DYSVSADDVARLTADAILANRLYILPHAAARERIRRRFERIDRTF

DEQAAEGWTH

-continued

SEQ ID NO: 14 ("MaADH_var13"):
MDGFLSGFDGVAAVVTGGASGIGLATATEMARRGARLVLSDVDQP

ALEQAVNGLRGQGFDAHGVVCDVRHLDEMVRLADEAFRLLGGVDV

VFSNAGIVVGGPIATMNHDDWRWVIDIDLWGSIHAVEAFLPRLLE

QGTGGHIAFNASFAGLVPVAGLGTYGVAKYGVVGLAETLAREVKP

NGIGVSVLCPMYVQTNLLSNSERIRGADGGPSGTPEGAFGPLPTQ

DYSVSADDVARLTADAILANRLYILPHAAARERIRRRFERIDRTF

DEQAAEGWTH

SEQ ID NO: 15 ("MaADH_var14"):
MDGFLSGFDGVAAVVTGGASGIGLATATEMARRGARLVLSDVDQP

ALEQAVNGLRGQGFDAHGVVCDVRHLDEMVRLADEAFRLLGGVDV

VFSNAGIVVGGPMAQMNHDDWRWVIDIDLWGSIHAVEAFLPRLLE

QGTGGHIAFNASFAGLVPVAGLGTYGVAKYGVVGLAETLAREVKP

NGIGVSVLCPMYVKTNLLSNSERIRGADGGRSGTPEGAFGPLPTQ

DYSVSADDVARLTADAILANRLYILPHAAARERIRRRFERIDRTF

DEQAAEGWTH

SEQ ID NO: 16 ("MaADH_var15"):
MDGFLSGFDGVAAWTGGASGIGLATATEMARRGARLVLSDVDQPA

LEQAVNGLRGQGFDAHGVVCDVRHLDEMVRLADEAFRLLGGVDVV

FSNAGIVVGGPMATMNHDDWRWVIDIDLWGSIHAVEAFLPRLLEQ

GTGGHIAFNASFAGLVPVAGLGTYGVAKYGVVGLAETLAREVKPN

GIGVSVLCPMYVKTNLLSNSERIRGADGGRSGTPEGAFGPLPTQD

YSVSADDVARLTADAILANRLYILPHAAARERIRRRFERIDRTFD

EQAAEGWTH

Results

The results of the bioconversion and acid treatment (when performed) are provided in Table 9 below. In particular, the table shows that following may be achieved: (i) low levels or an absence of the diol of compound (VII) from the bioconversion; (ii) relatively high levels of the (Z)-5-muscenone after acid treatment; and (ii) relatively high ee % of the R-enantiomer of (Z)-5-muscenone.

TABLE 9

| | Bioconversion | | | | | | Dehydration + rearrangement | | |
|---|---|---|---|---|---|---|---|---|---|
| Variant | Reaction cond. | 2 h conv. [% rpa] | Final conv. [% rpa] | EE + HK [% rpa] | Diol [% rpa] | time [h] | Acid | (Z)-5-Musc.[a] [% rpa] | % ee |
| MaADH | [I] | 5 | 71 | 68 + 3 | 0 | 90 | pTSA | 27 | 62 |
| MaADH_var1 | [I] | 6 | 86 | 83 + 2 | 1 | 120 | pTSA | 26 | 66 |
| MaADH_var2 | [I] | 1 | 61 | 59 + 1 | 1 | 120 | pTSA | 27 | 61 |
| MaADH_var3 | [I] | 3 | 60 | 58 + 1 | 1 | 90 | pTSA | 26 | 62 |
| MaADH_var4 | [II] | 23 | 86 | 82 + 3 | 1 | 28 | $H_3PO_4$ | 38 | 92 |
| MaADH_var5 | [II] | 13 | 81 | 78 + 3 | 0 | 28 | $H_3PO_4$ | 41 | 94 |
| MaADH_var6 | [II] | 7 | 86 | 81 + 2 | 3 | 28 | $H_3PO_4$ | 49 | 92 |
| MaADH_var7 | [III] | 8 | 89 | 86 + 0 | 3 | 69 | $H_3PO_4$ | 46 | 93 |
| MaADH_var8 | [III] | 7 | 94 | 94 + 0 | 0 | 69 | $H_3PO_4$ | 47 | 99 |
| MaADH_var9 | [III] | 11 | 97 | 97 + 0 | 0 | 45 | $H_3PO_4$ | 43 | 98 |
| MaADH_var10 | [III] | 16 | 92 | 88 + 1 | 3 | 29 | $H_3PO_4$ | 39 | 96 |
| MaADH_var11 | [III] | 26 | 94 | 89 + 1 | 4 | 26 | $H_3PO_4$ | 41 | 97 |
| MaADH_var12 | [III] | 8 | 94 | 94 + 0 | 0 | 49 | $H_3PO_4$ | 44 | 98 |
| MaADH_var12 | [IV] | 8 | 81 | 80 + 1 | 0 | 74 | — | n.d. | n.d. |
| MaADH_var13 | [IV] | 12 | 85 | 85 + 0 | 0 | 46 | $H_3PO_4$ | 41 | 96 |
| MaADH_var14 | [IV] | 13 | 84 | 84 + 0 | 0 | 47 | $H_3PO_4$ | 42 | 95 |

TABLE 9-continued

| | Bioconversion | | | | | | Dehydration + rearrangement | | |
|---|---|---|---|---|---|---|---|---|---|
| Variant | Reaction cond. | 2 h conv. [% rpa] | Final conv. [% rpa] | EE + HK [% rpa] | Diol [% rpa] | time [h] | Acid | (Z)-5-Musc.[a] [% rpa] | % ee |
| MaADH_var15 | [IV] | 13 | 85 | 85 + 0 | 0 | 47 | $H_3PO_4$ | 42 | 95 |
| MaADH_var13 | [V] | 12 | 84 | 84 + 0 | 0 | 70 | — | n.d. | n.d. |
| MaADH_var14 | [V] | 12 | 90 | 90 + 0 | 0 | 94 | — | n.d. | n.d. |
| MaADH_var15 | [V] | 12 | 84 | 84 + 0 | 0 | 94 | — | n.d. | n.d. |

[a]Ratio of (Z)-5-muscenone against other muscenone isomers
rpa = relative plot area, i.e. % of GC area
EE = enol ether (compound of formula (IV))
HK = hydroxy ketone (compound of formula (II))
Diol = compound of formula (VII)

The foregoing broadly describes certain embodiments of the present invention without limitation. Variations and modifications as will be readily apparent to those skilled in the art are intended to be within the scope of the present invention as defined in and by the appended claims.

The invention claimed is:

1. A method for making a mixture comprising a compound of formula (II), a compound of formula (III) and a compound of formula (IV), Formula (II)

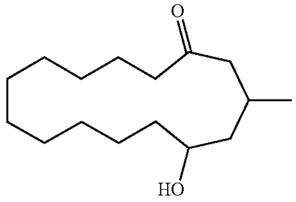

Formula (III)

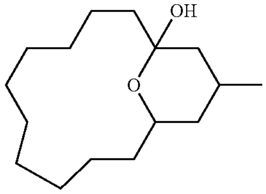

Formula (IV)

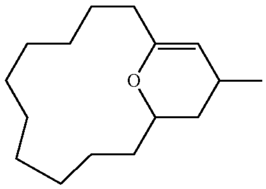

wherein the method comprises contacting a compound of formula (I) with an alcohol dehydrogenase, Formula (I)

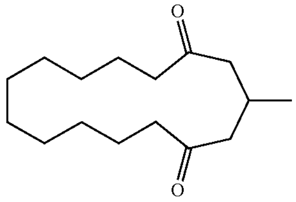

.

2. The method of claim 1, wherein the alcohol dehydrogenase has an amino acid sequence as set out in SEQ ID NO: 1 or is a variant of the amino acid sequence as set out in SEQ ID NO: 1, the variant having an amino acid sequence with at least 70% identity with the amino acid sequence as set out in SEQ ID NO: 1.

3. The method of claim 2, wherein the alcohol dehydrogenase is the variant of the amino acid sequence as set out in SEQ ID NO: 1, and the alcohol dehydrogenase variant includes an amino acid alteration relative to one or more of the following amino acids in the amino acid sequence as set out in SEQ ID NO: 1: R11, F30, V99, A100, L103, Q105, M106, L133, T145, N154, G161, V192, E194, K196, V198, Y209, M211, A213, E227 and S258.

4. The method according to claim 3, wherein the alcohol dehydrogenase variant has an amino acid sequence with at least 90% identity with the amino acid sequence as set out in SEQ ID NO: 1.

5. The method according to claim 1, wherein the alcohol dehydrogenase has an amino acid sequence as set out in any one of SEQ ID NO: 2 to SEQ ID NO: 16.

6. The method of claim 1, wherein the method takes place in the presence of an enzyme cofactor and a cofactor regeneration system.

7. The method of claim 1 further comprising treating the mixture with acid to provide one or more compound(s) of formula (V), Formula (V)

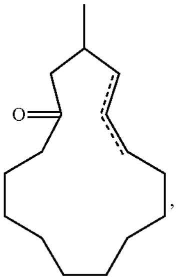

, wherein one of ------ is a single bond and the other is a double bond.

8. The method of claim 1 further comprising treating the mixture with acid to provide a mixture comprising a compound of formula (Va), a compound of formula (Vb), and a compound of formula (Vc), Formula (Va)

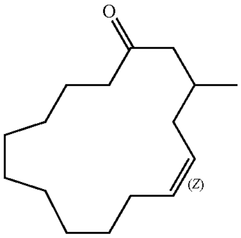

Formula (Vb)

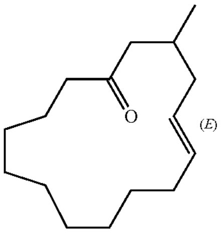

Formula (Vc)

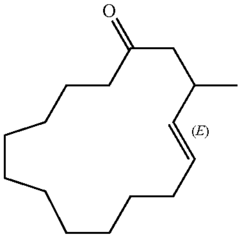

.

9. The method of claim 8, wherein the mixture comprising a compound of formula (Va), a compound of formula (Vb), and a compound of formula (Vc) further comprises a compound of Formula (Vd), Formula (Vd)

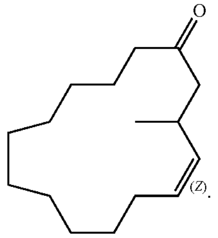

10. The method of claim 8, wherein the mixture comprising a compound of formula (Va), a compound of formula (Vb), and a compound of formula (Vc) does not comprise a compound of Formula (Vd), Formula (Vd)

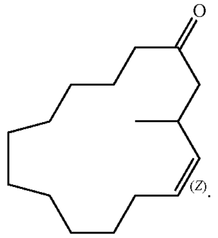

11. The method of claim 7, wherein the acid is para-toluene sulphonic acid (pTSA), phosphoric acid, or combinations thereof.

12. The method of claim 7 further comprising an enrichment distillation step after the acid treatment to obtain a desired stereoisomer ratio.

13. A composition comprising a compound of formula (II), a compound of formula (III) and a compound of formula (IV), Formula (II)

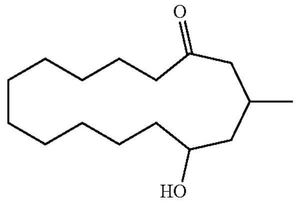

Formula (III)

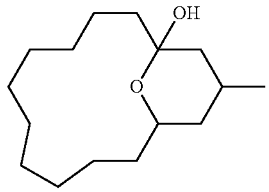

Formula (IV)

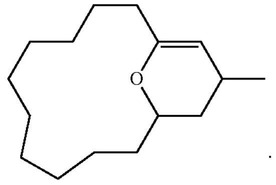

14. A composition comprising a compound of formula (Va), a compound of formula (Vb) and a compound of formula (Vc), Formula (Va)

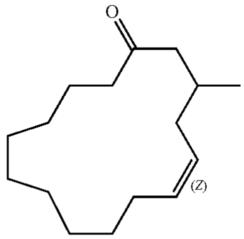

Formula (Vb)

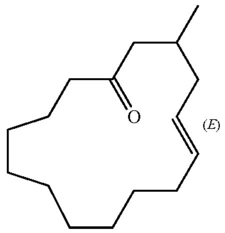

Formula (Vc)

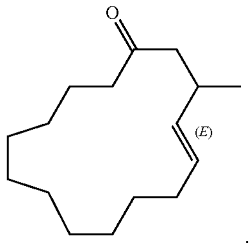

wherein:

the compound of formula (Va) is present in the composition in an amount ranging from about 20.0 wt % to less than about 40.0 wt %;

the compound of formula (Vb) is present in the composition in an amount ranging from greater than about 40.0 wt % to about 70.0 wt %; and the compound of formula (Vc) is present in the composition in an amount ranging from about 5.0 wt % to about 15.0 wt %.

15. The composition of claim 14, wherein at least one of:

the compound of formula (Va) has an enantiomeric excess of the (R) enantiomer equal to or greater than about 25.0%;

the compound of formula (Vb) has an enantiomeric excess of the (R) enantiomer equal to or greater than about 25.0%; or the compound of formula (Vc) has an enantiomeric excess of the(S) enantiomer equal to or greater than about 25.0%.

16. The composition of claim 14, wherein at least one of:

the compound of formula (Va) has an enantiomeric excess of the (R) enantiomer equal to or greater than about 60.0%;

the compound of formula (Vb) has an enantiomeric excess of the (R) enantiomer equal to or greater than about 60.0%; or the compound of formula (Vc) has an enantiomeric excess of the(S) enantiomer equal to or greater than about 60.0%.

17. The composition of claim 14, wherein the composition further comprises a compound of formula (Vd) in an amount ranging from about 0.5 wt % to about 5.0 wt %, Formula (Vd)

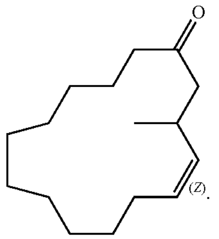

18. A composition comprising:

from 35 to 55% w/w of a compound of formula (Va) having an enantiomeric excess of the (R) enantiomer of less than 80%;

Formula (Va)

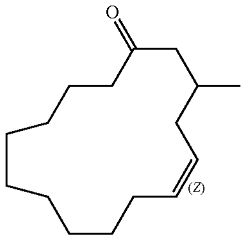

from 27 to 40% w/w of a compound of formula (Vb) having an enantiomeric excess of the (R) enantiomer of less than 80%;

Formula (Vb)

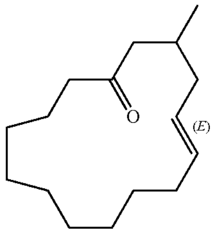

from 3 to 20% w/w of a compound of formula (Vc) having an enantiomeric excess of the(S) enantiomer of less than 80%; and Formula (Vc)

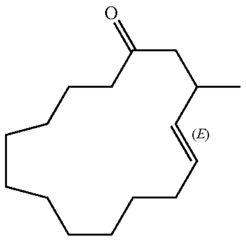

from 0 to 5% w/w of a compound of formula (Vd) having an enantiomeric excess of the(S) enantiomer of less than 80%

Formula (Vd)

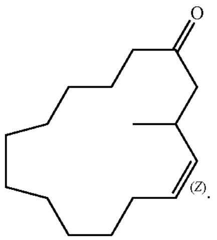

19. A composition obtained by the method of claim 1.

20. A method of using the composition of claim 13 as a fragrance ingredient, wherein the method comprises adding the composition to a consumer product.

21. A consumer product comprising the composition of claim 13.

22. An alcohol dehydrogenase, wherein the alcohol dehydrogenase is a variant of the alcohol dehydrogenase having the amino acid sequence as set out in SEQ ID NO: 1, wherein the variant has at least 70% sequence identity with SEQ ID NO: 1.

* * * * *